US011771797B2

(12) United States Patent
Aviles

(10) Patent No.: US 11,771,797 B2
(45) Date of Patent: Oct. 3, 2023

(54) ABSORBENT ARTICLE WITH TOPSHEET TREATED TO REDUCE SURFACTANT MIGRATION

(71) Applicant: The Procter & Gamble Company, Cincinnati, OH (US)

(72) Inventor: Misael Omar Aviles, Hamilton, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 1131 days.

(21) Appl. No.: 16/452,903

(22) Filed: Jun. 26, 2019

(65) Prior Publication Data

US 2019/0388578 A1  Dec. 26, 2019

Related U.S. Application Data

(60) Provisional application No. 62/689,909, filed on Jun. 26, 2018.

(51) Int. Cl.
*A61F 13/513* (2006.01)
*A61L 15/48* (2006.01)
(Continued)

(52) U.S. Cl.
CPC ............ *A61L 15/48* (2013.01); *A61F 13/513* (2013.01); *A61F 13/514* (2013.01);
(Continued)

(58) Field of Classification Search
CPC .......... A61F 13/15203; A61F 13/51113; A61F 13/513; A61F 13/51305; A61F 2013/1556;
(Continued)

(56) References Cited

U.S. PATENT DOCUMENTS 3,156,242 A   11/1964   Crowe, Jr.
3,881,489 A   5/1975    Hartwell
(Continued)

FOREIGN PATENT DOCUMENTS

EP   0710472 A1   5/1996
JP   2004033325 A   2/2004
(Continued)

OTHER PUBLICATIONS

International Search Report, PCT/US2019/039188, dated Sep. 30, 2019, 14 pages.

*Primary Examiner* — Catharine L Anderson
(74) *Attorney, Agent, or Firm* — Sarah M. DeCristofaro; William E. Gallagher

(57) ABSTRACT

An absorbent article having a liquid pervious topsheet wherein at least a portion of the topsheet has been treated to become hydrophobic; a backsheet joined to said topsheet; an absorbent core disposed between said topsheet and said backsheet, said absorbent core having an inner surface oriented toward the skin of the wearer when said absorbent article is being worn and an outer surface oriented toward the garment of the wearer when said absorbent article is being worn; and a surfactant applied to at least a portion of said outer surface of said topsheet wherein the topsheet has been treated hydrophobic and wherein the hydrophilic surfactant is added to the areas treated hydrophobic.

11 Claims, 15 Drawing Sheets

(51) Int. Cl.
*A61F 13/514* (2006.01)
*A61F 13/53* (2006.01)
*A61L 15/34* (2006.01)
*A61F 13/511* (2006.01)
*A61F 13/15* (2006.01)
*A61F 13/51* (2006.01)

(52) U.S. Cl.
CPC ........ *A61F 13/51113* (2013.01); *A61F 13/53* (2013.01); *A61L 15/34* (2013.01); *A61F 2013/15837* (2013.01); *A61F 2013/51059* (2013.01)

(58) Field of Classification Search
CPC .. A61F 2013/51059; A61F 2013/51061; A61F 2013/51066; A61F 2013/51069; A61F 2013/51355; A61F 2013/51366; A61L 15/34; A61L 15/48
See application file for complete search history.

(56) References Cited

U.S. PATENT DOCUMENTS

| | | | |
|---|---|---|---|
| 3,929,135 A | 12/1975 | Thompson | |
| 3,978,185 A | 8/1976 | Buntin | |
| 3,989,867 A | 11/1976 | Sisson | |
| 4,324,246 A | 4/1982 | Mullane et al. | |
| 4,341,216 A | 7/1982 | Obenour | |
| 4,342,314 A | 8/1982 | Radel et al. | |
| 4,463,045 A | 7/1984 | Ahr et al. | |
| 4,578,414 A | 3/1986 | Sawyer | |
| 4,591,523 A | 5/1986 | Thompson et al. | |
| 4,609,518 A | 9/1986 | Curro et al. | |
| 4,629,643 A | 12/1986 | Curro et al. | |
| 4,695,422 A | 9/1987 | Curro | |
| 4,713,068 A | 12/1987 | Wang | |
| 4,818,600 A | 4/1989 | Braun | |
| 4,839,216 A | 6/1989 | Curro | |
| 4,950,264 A | 8/1990 | Osborn, III | |
| 4,988,344 A | 1/1991 | Reising et al. | |
| 4,988,345 A | 1/1991 | Reising | |
| 5,006,394 A | 4/1991 | Baird | |
| 5,137,537 A | 8/1992 | Herron | |
| 5,183,707 A | 2/1993 | Herron | |
| 5,190,563 A | 3/1993 | Herron | |
| 5,643,588 A | 7/1997 | Roe et al. | |
| 5,665,452 A | 9/1997 | Langdon | |
| 5,792,404 A | 8/1998 | Cree | |
| 5,885,265 A | 3/1999 | Osborn, III | |
| 6,025,535 A | 2/2000 | Octavio | |
| 6,186,992 B1 | 2/2001 | Roe et al. | |
| 6,548,732 B2 | 4/2003 | Erdman | |
| 6,623,464 B2 | 9/2003 | Bewick-sonntag | |
| 6,624,341 B1 | 9/2003 | Depner | |
| 6,664,439 B1 | 12/2003 | Arndt | |
| 7,172,801 B2 | 2/2007 | Hoying | |
| 7,402,723 B2 | 7/2008 | Stone | |
| 7,407,899 B2 | 8/2008 | Wang | |
| 7,410,683 B2 | 8/2008 | Curro | |
| 7,553,532 B2 | 6/2009 | Turner | |
| 7,648,752 B2 | 1/2010 | Hoying et al. | |
| 7,655,176 B2 | 2/2010 | Stone | |
| 7,785,690 B2 | 8/2010 | Turner | |
| 8,124,827 B2 | 2/2012 | Tamburro | |
| 8,313,792 B2 | 11/2012 | Tee, Jr. et al. | |
| 8,440,286 B2 | 5/2013 | Curro | |
| 8,614,365 B2 | 12/2013 | Hammons | |
| 8,674,169 B2 | 3/2014 | Brennan | |
| 8,728,049 B2 | 5/2014 | Hammons | |
| 9,364,859 B2 | 6/2016 | Qin | |
| 10,195,091 B2* | 2/2019 | Rosati | D04H 1/42 |
| 10,238,553 B2* | 3/2019 | Day | A61F 13/5123 |
| 10,271,997 B2* | 4/2019 | Arizti | A61F 13/511 |
| 2001/0025162 A1 | 9/2001 | Roe | |
| 2001/0027303 A1 | 10/2001 | Bewick-sonntag | |
| 2002/0064639 A1 | 5/2002 | Rearick | |
| 2002/0147433 A1* | 10/2002 | McOsker | A61L 15/46 604/385.01 |
| 2003/0055394 A1* | 3/2003 | Gibbs | A61F 13/5633 604/389 |
| 2007/0219515 A1 | 9/2007 | Marsh et al. | |
| 2010/0221407 A1 | 9/2010 | Tee, Jr. | |
| 2010/0228209 A1 | 9/2010 | Carlucci | |
| 2010/0262104 A1 | 10/2010 | Carlucci | |
| 2011/0268932 A1* | 11/2011 | Catalan | A61L 15/20 442/79 |
| 2012/0071847 A1 | 3/2012 | Bewick-sonntag | |
| 2012/0089110 A1 | 4/2012 | Pan | |
| 2014/0336605 A1 | 11/2014 | Hardie et al. | |
| 2015/0038933 A1 | 2/2015 | Day | |
| 2015/0282999 A1* | 10/2015 | Arizti | A61F 13/8405 604/385.01 |
| 2015/0376384 A1* | 12/2015 | Maldonado | C08L 23/06 604/367 |
| 2016/0067118 A1 | 3/2016 | Hammons et al. | |
| 2016/0167334 A1 | 6/2016 | Arora | |
| 2018/0071151 A1 | 3/2018 | Aviles | |
| 2018/0071156 A1 | 3/2018 | Rosati | |
| 2018/0098889 A1 | 4/2018 | Hardie | |
| 2020/0316245 A1 | 10/2020 | Richards et al. | |

FOREIGN PATENT DOCUMENTS

| | | |
|---|---|---|
| WO | WO97/24097 A1 | 7/1997 |
| WO | 0236177 A2 | 5/2002 |
| WO | 2009152021 A2 | 12/2009 |

* cited by examiner

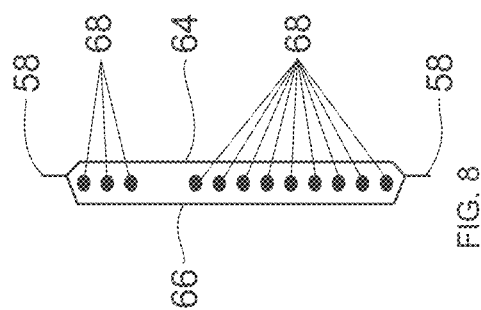
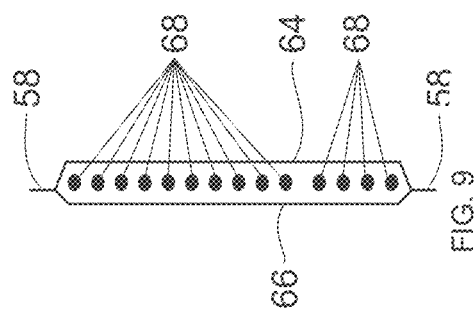
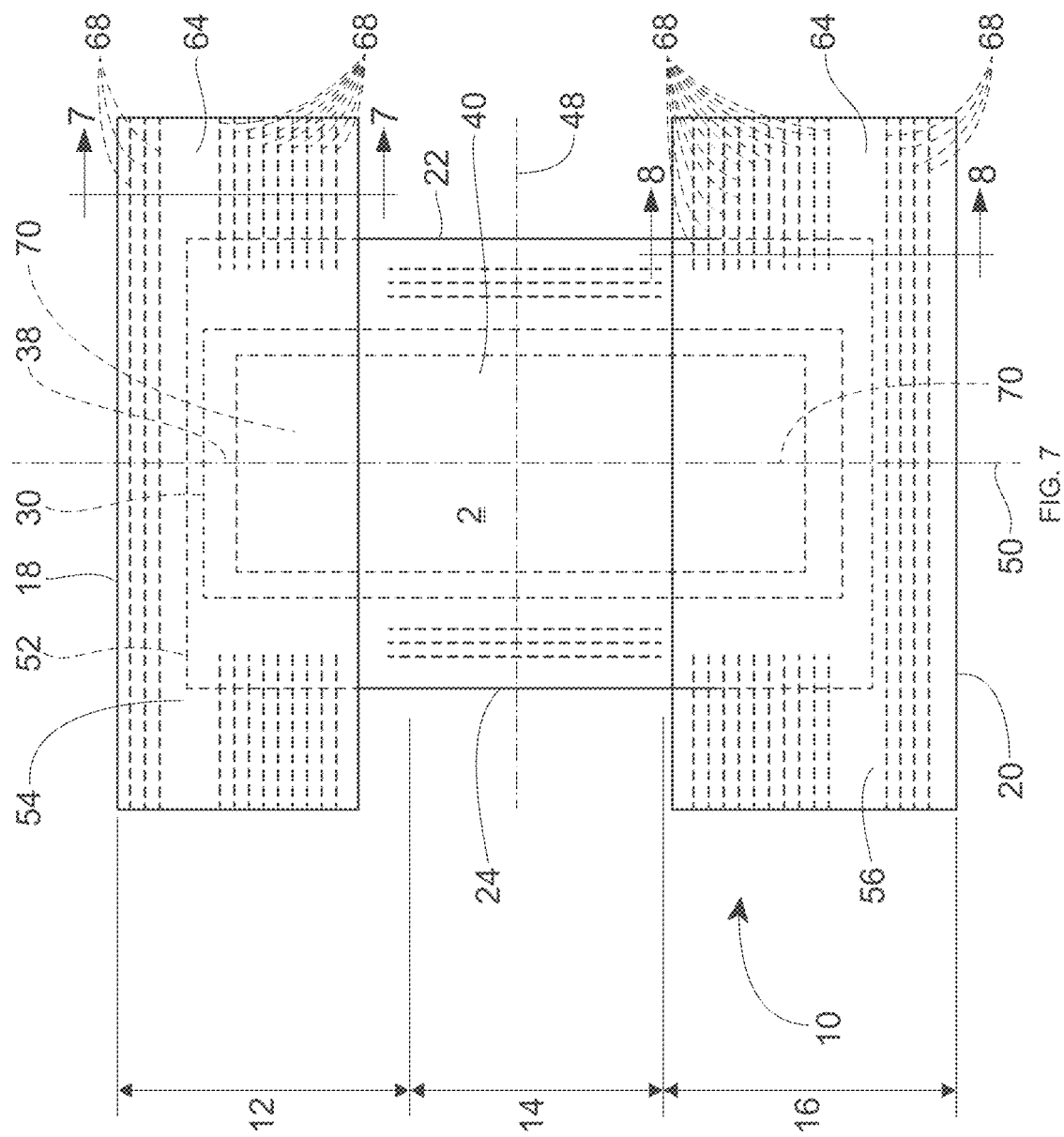

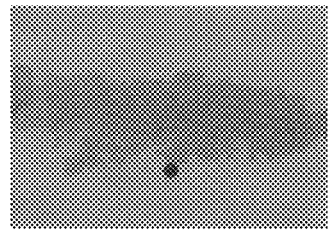
FIG. 10A
T=0 (1 day after print)
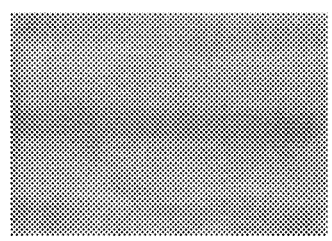
FIG. 10B
Fresh Insult
Bicomponent Sample
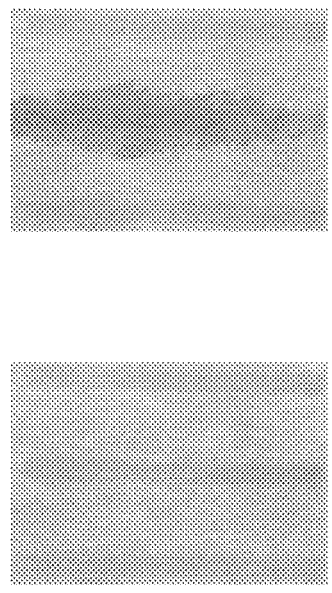
FIG. 10C
T = 1 Month (40C/75RH)
FIG. 10D
Aged Insult T=0 (1 day after print)

Fresh Insult

T = 1 Month (40C/75RH)

Aged Insult

Bicomponent + GTS Sample

Bicomponent + WR1300 Sample
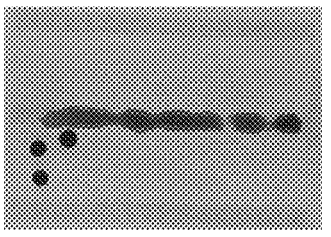
FIG. 12A
T=0 (1 day after print)
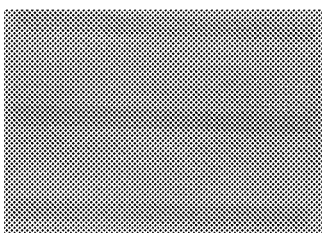
FIG. 12B
Fresh Insult
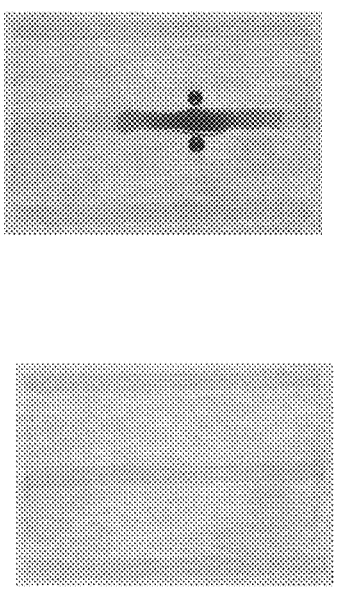
FIG. 12C
T = 1 Month (40C/75RH)
FIG. 12D
Aged Insult

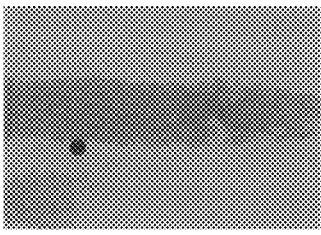
FIG. 13D
Aged Insult
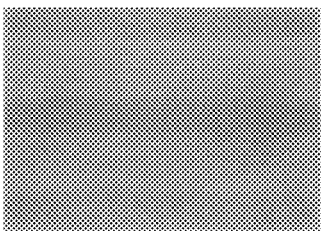
FIG. 13C
T= 1 Month (40C/75RH)
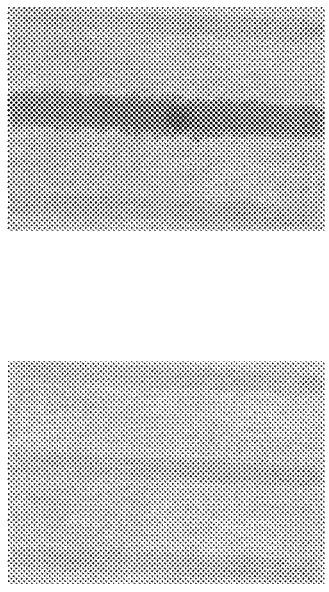
Bicomponent + R812 Sample
FIG. 13B
Fresh Insult
FIG. 13A
T=0 (1 day after print)

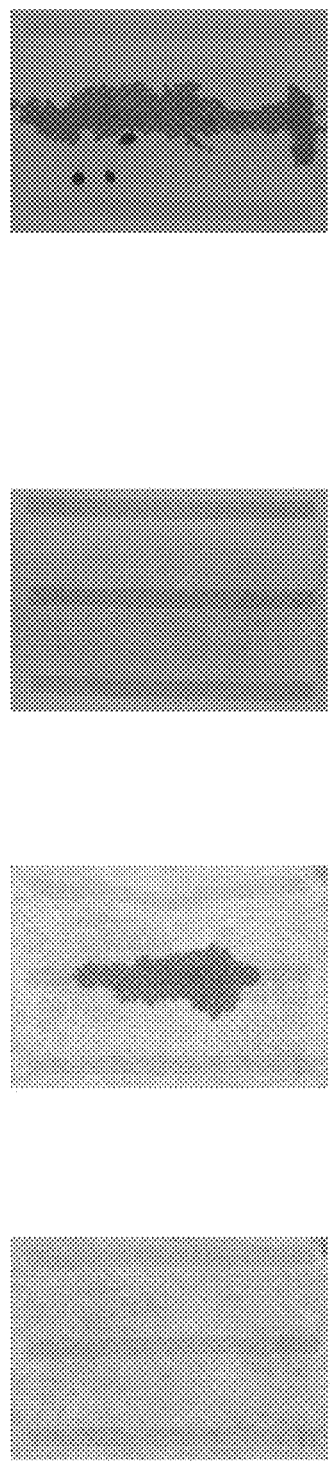

Polypropylene + Erucamide Sample
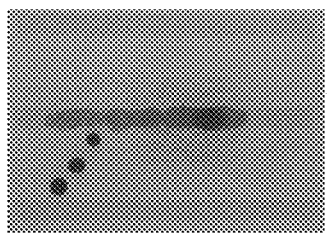
T=0 (1 day after print)
FIG. 15A
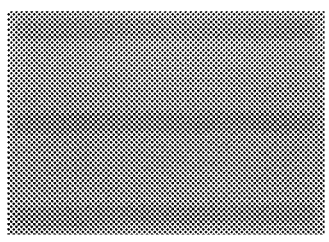
Fresh Insult
FIG. 15B
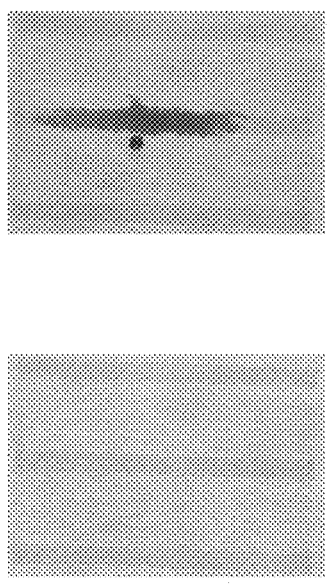
T = 1 Month (40C/75RH)
FIG. 15C
Aged Insult
FIG. 15D Example ToFSIMS Pattern Binary Image Example ToFSIMS Pattern 8bit Grayscale Image Example Stained Pattern 8bit Grayscale Image Example Stained Pattern Binary Image

ABSORBENT ARTICLE WITH TOPSHEET TREATED TO REDUCE SURFACTANT MIGRATION

RELATED APPLICATIONS

This applications claims the benefit of U.S. Provisional Application No. 62/689,909, filed Jun. 26, 2018, the substance of which is incorporated herein by reference.

FIELD OF INVENTION

This application relates to absorbent articles, including catamenial devices such as sanitary napkins for the absorption of menses, diapers, and articles used for adult incontinence. More particularly, the present invention relates to absorbent articles including a topsheet that improves upon surfactant migration.

BACKGROUND OF THE INVENTION

Disposable absorbent articles, such as diapers, training pants, adult incontinence, and catamenial devices or sanitary pads are known.

Treatments to the bodyside surface of the topsheet of diaper absorbent products have been proposed to primarily provide skin health benefits and secondarily to allow fluid such as urine to be absorbed into the product. Treatments of the bodyside surface of the topsheet of feminine hygiene products have also been proposed to provide skin health benefits and similarly the treatment deployment is generally performed to minimize the hindrance of menstrual fluid acquisition. Treatments are often applied uniform in either composition or distribution. Many of these treatments include and rely upon the use of surfactants. However, once placed on the surface, migration of the surfactant often occurs from the desired area.

As such, it would be beneficial to find a means by which surfactant migration could be reduced such that the surfactant remains where it was placed.

SUMMARY OF THE INVENTION

An absorbent article having a liquid pervious topsheet, said topsheet having an inner surface oriented toward the interior of said absorbent article and an outer surface oriented toward the skin of the wearer is disclosed. At least a portion of the topsheet has been treated to become hydrophobic. The absorbent article additionally has a backsheet joined to said topsheet and an absorbent core disposed between said topsheet and said backsheet. A surfactant is applied to at least a portion of said outer surface of said topsheet wherein the topsheet has been treated hydrophobic and wherein the hydrophilic surfactant is added to the areas treated hydrophobic.

A method of limiting surfactant migration on a topsheet is further disclosed. The method includes providing a nonwoven including a hydrophobic coating treatment or including a hydrophobic melt additive and treating the portions of the topsheet treated with the hydrophobic coating treatment or the hydrophobic melt additive with a surfactant.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

FIG. 7 is a plan view of the pant, laid flat, with a garment-facing surface facing the viewer.

FIG. 8 is a cross-sectional view of a front belt portion taken about line 7-7 of FIG. 7.

FIG. 9 is a cross-sectional view of a back belt portion taken about line 8-8 of FIG. 7.

FIG. 10A-D are grayscale images of a Bicomponent topsheet with and without insult.

FIG. 12A-D are grayscale images of a Bicomponent topsheet with a WR1300 additive with and without insult.

FIG. 13A-D are grayscale images of a Bicomponent topsheet with an AEROSIL® R 812 additive with and without insult.

FIG. 14A-D are grayscale images of a Polypropylene topsheet with and without insult.

FIG. 15A-D are grayscale images of a Polypropylene topsheet with a Erucamide additive with and without insult.

DETAILED DESCRIPTION OF EXAMPLES

The present invention is directed to absorbent articles, particularly disposable absorbent articles, including a topsheet that includes a web including both hydrophilic surfactant coated onto fibers including a hydrophobic treatment. Disposable absorbent articles can be baby diapers or feminine hygiene articles, including incontinence devices and catamenial products such as tampons, sanitary napkins, pantiliners, interlabial products, and the like. The invention is disclosed below with respect to one embodiment of a catamenial device, such as a sanitary napkin or pantiliner.

Absorbent Article

Figure 1:
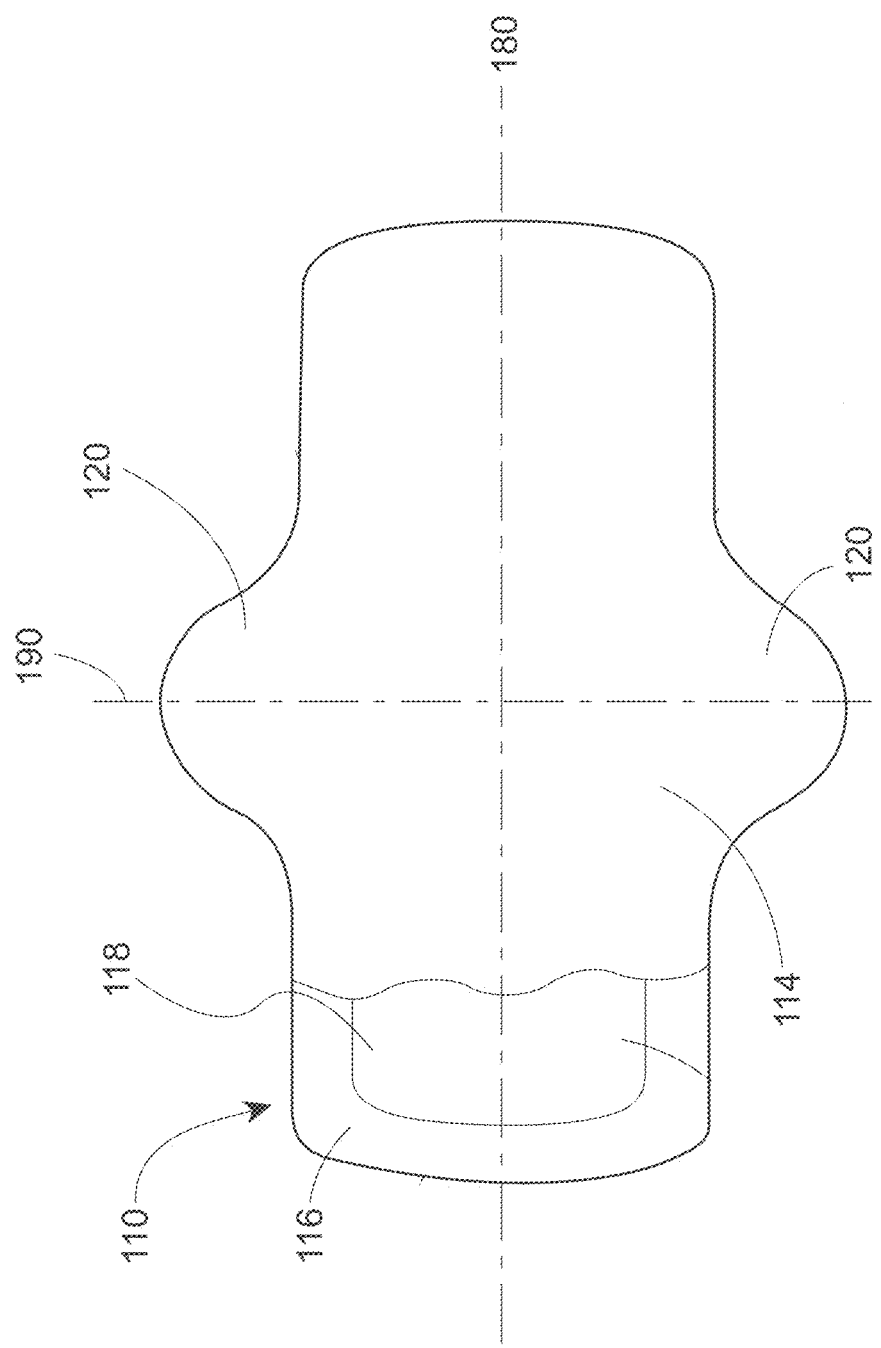
FIG. 1 is a plan view of an example absorbent article of the present disclosure that is a sanitary napkin.

FIG. 1 shows an absorbent article 110, that can be a sanitary napkin or pantiliner, having a body-contacting surface 120 including the outer surface of a topsheet 114, a liquid impervious backsheet 116 joined to the topsheet 114, an absorbent core 118. The sanitary napkin 110 has a longitudinal axis 180, a transverse axis 190 and may also be provided with additional features commonly found in napkins, including "wings" or "flaps" (not shown) as is known in the art, and, and/or a secondary topsheet, and/or a fluid acquisition layer, and/or other layers designed to promote fluid transport to the absorbent core 18. Likewise, the topsheet of the sanitary napkin can have various optional characteristics, as is known in the art. For example, the topsheet 14 can have channels embossed therein to direct fluid flow, and can have apertures there through to aid in fluid acquisition, and can have printed signals visible on or through, the visible signals being printed on the topsheet or underlying layers, and visible for functional and aesthetic properties.

The catamenial devices 10 of FIG. 1 has a surfactant composition 22 applied thereto. The catamential device 10 of FIG. 1 has a surfactant composition 22 applied in parallel stripes. Surfactant may be applied in any random or organized pattern to the topsheet including, for example, strips, dots, circles, or a spray coating.

Topsheet

The absorbent article may include any known or otherwise effective topsheet, such as one which is compliant, soft feeling, and non-irritating to the wearer's skin. Suitable topsheet materials include a liquid pervious material that is oriented towards and contacts the body of the wearer permitting bodily discharges to rapidly penetrate through it without allowing fluid to flow back through the topsheet to the skin of the wearer. A suitable topsheet can be made of various materials such as woven and nonwoven materials; apertured film materials including apertured formed thermoplastic films, apertured plastic films, and fiber-entangled apertured films; hydro-formed thermoplastic films; porous foams; reticulated foams; reticulated thermoplastic films; thermoplastic scrims; or combinations thereof.

Apertured film materials suitable for use as the topsheet include those apertured plastic films that are non-absorbent and pervious to body exudates and provide for minimal or no flow back of fluids through the topsheet. Nonlimiting examples of other suitable formed films, including apertured and non-apertured formed films, are more fully described in U.S. Pat. No. 3,929,135, issued to Thompson on Dec. 30, 1975; U.S. Pat. No. 4,324,246, issued to Mullane et al. on Apr. 13, 1982; U.S. Pat. No. 4,342,314, issued to Radel et al. on Aug. 3, 1982; U.S. Pat. No. 4,463,045, issued to Ahr et al. on Jul. 31, 1984; U.S. Pat. No. 5,006,394, issued to Baird on Apr. 9, 1991; U.S. Pat. No. 4,609,518, issued to Curro et al. on Sep. 2, 1986; and U.S. Pat. No. 4,629,643, issued to Curro et al. on Dec. 16, 1986. Commercially available formed filmed topsheets include those topsheet materials marketed by the Procter & Gamble Company (Cincinnati, Ohio) under the trade name DRI-WEAVE.

Nonlimiting examples of woven and nonwoven materials suitable for use as the topsheet include fibrous materials made from natural fibers, modified natural fibers, synthetic fibers, or combinations thereof. These fibrous materials can be either hydrophilic or hydrophobic, but it is preferable that the topsheet be hydrophobic or rendered hydrophobic. As an option portions of the topsheet can be rendered hydrophilic, by the use of any known method for making topsheets containing hydrophilic components. One such method include treating an apertured film component of a nonwoven/apertured thermoplastic formed film topsheet with a surfactant as described in U.S. Pat. No. 4,950,264, issued to Osborn on Aug. 21, 1990. Other suitable methods describing a process for treating the topsheet with a surfactant are disclosed in U.S. Pat. Nos. 4,988,344 and 4,988,345, both issued to Reising et al. on Jan. 29, 1991. The topsheet may have hydrophilic fibers, hydrophobic fibers, or combinations thereof.

A particularly preferred topsheet includes staple length polypropylene fibers having a denier of about 1.5, such as Hercules type 151 polypropylene marketed by Hercules, Inc. of Wilmington, Del. As used herein, the term "staple length fibers" refers to those fibers having a length of at least about 15.9 mm (0.62 inches).

When the topsheet includes a nonwoven fibrous material in the form of a nonwoven web, the nonwoven web may be produced by any known procedure for making nonwoven webs, nonlimiting examples of which include spunbonding, carding, wet-laid, air-laid, meltblown, needle-punching, mechanical entangling, thermo-mechanical entangling, and hydroentangling. A specific example of a suitable meltblown process is disclosed in U.S. Pat. No. 3,978,185, to Buntin et al., issued Aug. 31, 1976. The nonwoven may be compression resistant as described in U.S. Pat. No. 7,785,690 entitled "Compression Resistant Nonwovens" issued on Aug. 31, 2010. The nonwoven web may have loops as described in U.S. Pat. No. 7,838,099 entitled "Looped Nonwoven Web" issued on Nov. 23, 2010.

Other suitable nonwoven materials include low basis weight nonwovens, that is, nonwovens having a basis weight of from about 18 $g/m^2$ to about 25 $g/m^2$. Suitable nonlimiting examples are described in U.S. Pat. Nos. 5,792,404 and 5,665,452.

The topsheet may include tufts as described in U.S. Pat. No. 8,728,049 entitled "Absorbent Article Having a Tufted Topsheet" issued on May 20, 2014, U.S. Pat. No. 7,553,532 entitled "Tufted Fibrous Web" issued on Jun. 30, 2009, U.S. Pat. No. 7,172,801 entitled "Tufted Laminate Web" issued on Feb. 6, 2007, or U.S. Pat. No. 8,440,286 entitled "Capped Tufted Laminate Web" issued on May 14, 2013. The topsheet may have an inverse textured web as described in U.S. Pat. No. 7,648,752 entitled "Inverse Textured Web" issued on Jan. 19, 2010. Tufts are also described in U.S. Pat. No. 7,410,683 entitled "Tufted Laminate Web" issued on Aug. 12, 2008.

The topsheet may have a pattern of discrete hair-like fibrils as described in U.S. Pat. No. 7,655,176 entitled "Method of Making a Polymeric Web Exhibiting A Soft and Silky Tactile Impression" issued on Feb. 2, 2010 or U.S. Pat. No. 7,402,723 entitled "Polymeric Web Exhibiting A Soft And Silky Tactile Impression" issued on Jul. 22, 2008.

The topsheet may include one or more structurally modified zones as described in U.S. Pat. No. 8,614,365 entitled "Absorbent Article" issued on Dec. 24, 2013. The topsheet may have one or more out of plane deformations as described in U.S. Pat. No. 8,704,036 entitled "Sanitary Napkin for Clean Body Benefit" issued on Apr. 22, 2014. The topsheet may have a masking composition as described in U.S. Pat. No. 6,025,535 entitled "Topsheet For Absorbent Articles Exhibiting Improved Masking Properties" issued on Feb. 15, 2000.

Absorbent Core

The absorbent core may be any absorbent means capable of absorbing or retaining liquids (e.g., menses and/or urine). The absorbent core may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester or polyolefin fibers; peat moss; tissue including tissue wraps and tissue laminates; absorbent foams; absorbent sponges; superabsorbent polymers; absorbent gelling materials; or any equivalent material or combinations of materials, or mixtures of these. The absorbent core may have more than one layer wherein each layer may be identical or distinct in one or more property or composition from another layer. A particularly preferred absorbent core is made of thermally bonded airlaid material having less than 50 percent synthetic fibers. Synthetic fibers are preferred due to the ease with which they fuse together to join the core and topsheet as described below. A particularly preferred synthetic fiber is a bi-component material having a polyethylene sheath and a polypropylene center.

The configuration and construction of the absorbent core may also be varied (e.g., the absorbent core may have varying caliper zones (e.g., profiled so as to be thicker in the center), hydrophilic gradients, superabsorbent gradients, or lower density and lower average basis weight acquisition zones; or may include one or more layers or structures). The total absorbent capacity of the absorbent core should, however, be compatible with the design loading and the intended use of the sanitary napkin. Further, the size and absorbent capacity of the absorbent core may be varied to accommodate different uses such as incontinence pads, panty liners, regular sanitary napkins, or overnight sanitary napkins.

The fluid absorbent material can be constructed from any of a variety of materials commonly used in disposable absorbent articles. Examples of suitable absorbent materials include creped cellulose wadding, cotton fluff, and citric acid cross-linked cellulose pulp disclosed in U.S. Pat. No. 5,190,563, issued Mar. 2, 1993, U.S. Pat. No. 5,183,707, issued Feb. 2, 1993; and U.S. Pat. No. 5,137,537, issued Aug. 11, 1992, all issued to Herron et al.; synthetic fibers disclosed in U.S. Pat. No. 4,578,414, Sawyer, issued Mar. 25, 1986; absorbent foams, absorbent sponges, superabsorbent composites, superabsorbent foam, and super absorbent polymers. A preferred fluid absorbent material is comminuted and airlaid wood pulp fibers commonly referred to as absorbent fluff. An absorbent fluff having a density of from about 0.05 g to about 0.175 g per $cm^3$ is generally acceptable.

The absorbent core structure may include a substrate and superabsorbent polymer layer as those described in U.S. Pat. No. 8,124,827 filed on Dec. 2, 2008 (Tamburro); U.S. application Ser. No. 12/718,244 published on Sep. 9, 2010; U.S. application Ser. No. 12/754,935 published on Oct. 14, 2010; or U.S. Pat. No. 8,674,169 issued on Mar. 18, 2014.

Backsheet

The backsheet acts as a barrier to any absorbed bodily fluids that may pass through the absorbent core to the garment surface thereof with a resulting reduction in risk of staining undergarments or other clothing. Further, the barrier properties of the backsheet permit manual removal, if a wearer so desires, of the interlabial absorbent article with reduced risk of hand soiling. A preferred material is a soft, smooth, compliant, liquid and vapor pervious material that provides for softness and conformability for comfort, and is low noise producing so that movement does not cause unwanted sound.

The backsheet may include a wet laid fibrous assembly having a temporary wet strength resin incorporated therein as described in U.S. Pat. No. 5,885,265 (Osborn, III.) issued Mar. 23, 1999. The backsheet may further be coated with a water resistant resinous material that causes the backsheet to become impervious to bodily fluids without impairing the spreading of adhesive materials thereon.

Another suitable backsheet material is a polyethylene film having a thickness of from about 0.012 mm (0.5 mil) to about 0.051 mm (2.0 mils). The backsheet may be embossed and/or matte finished to provide a more clothlike appearance. Further, the backsheet may permit vapors to escape from the absorbent core 42 (i.e., the backsheet is breathable) while still preventing body fluids from passing through the backsheet. A preferred microporous polyethylene film is available from Tredegar Corporation, Virginia, USA, under Code No. XBF-1 12W.

Suitable breathable backsheets for use herein include all breathable backsheets known in the art. In principle there are two types of breathable backsheets, single layer breathable backsheets which are breathable and impervious to liquids and backsheets having at least two layers, which in combination provide both breathability and liquid imperviousness. Suitable single layer breathable backsheets for use herein include those described for example in GB A 2184 389, GB A 2184 390, GB A 2184 391, U.S. Pat. Nos. 4,591,523, 3,989,867, 3,156,242 and WO 97/24097.

The backsheet may have two layers: a first layer including a gas permeable aperture formed film layer and a second layer including a breathable microporous film layer as described in U.S. Pat. No. 6,462,251 (Cimini) issued Oct. 8, 2002. Suitable dual or multi layer breathable backsheets for use herein include those exemplified in U.S. Pat. Nos. 3,881,489; 4,341,216; 4,713,068; 4,818,600, EP 203 821, EP 710 471, EP 710 472, and EP 793 952.

The backsheet may be vapor permeable as described in U.S. Pat. No. 6,623,464 (Bewick-Sonntag) issued Sep. 23, 2003 or U.S. Pat. No. 6,664,439 (Arndt) issued Dec. 16, 2003. The backsheet can be formed from any vapor permeable material known in the art. Backsheet can be a microporous film, an apertured formed film, or other polymer film that is vapor permeable, or rendered to be vapor permeable, as is known in the art.

The backsheet can be typically positioned adjacent the outer-facing surface of the absorbent core and can be joined thereto by any suitable attachment device known in the art. For example, the backsheet may be secured to the absorbent core by a uniform continuous layer of adhesive, a patterned layer of adhesive, or an array of separate lines, spirals, or spots of adhesive.

The absorbent article may also include such other suitable features as are known in the art including, but not limited to, re-closable fastening system, lotion, acquisition layers, distribution layers, wetness indicators, sensors, elasticized waist bands and other similar additional elastic elements and the like, belts and the like, waist cap features, containment and aesthetic characteristics and combinations thereof.

Diaper/Pant

Figure 2:
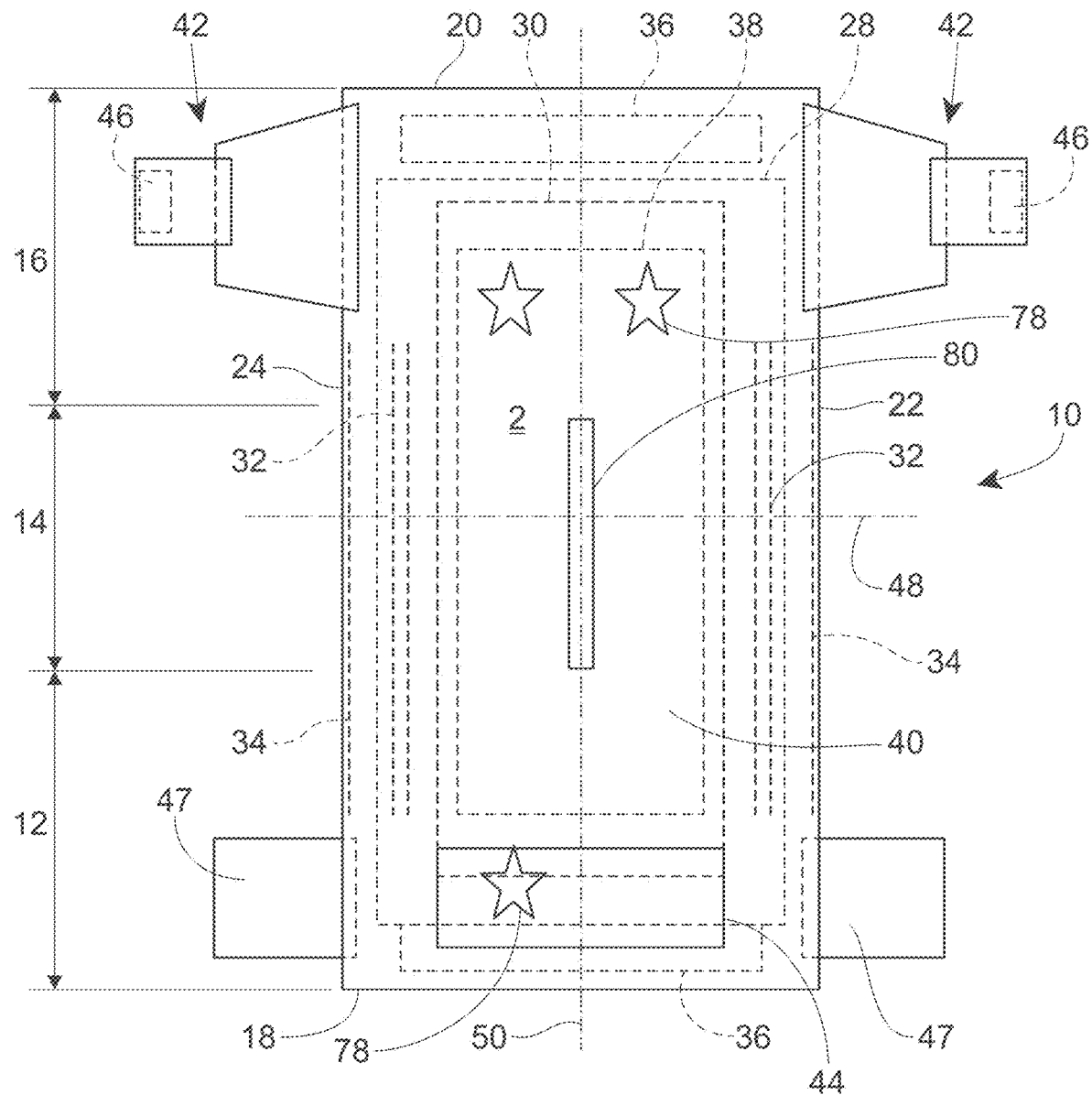
FIG. 2 is a plan view of an example diaper, garment-facing surface facing the viewer, in a flat laid-out state.
Figure 3:
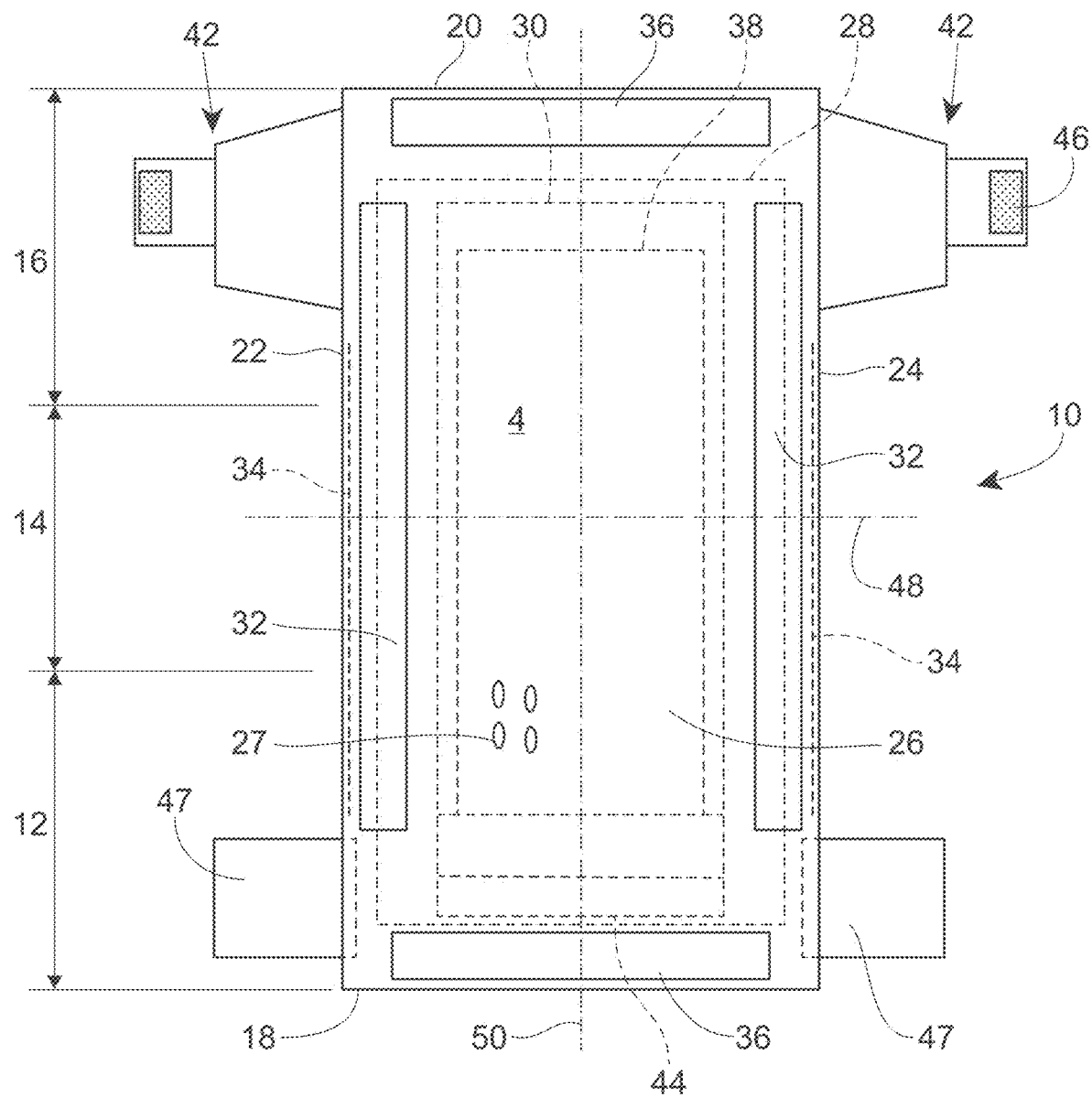
FIG. 3 is a plan view of the example diaper of FIG. 2, wearer-facing surface facing the viewer, in a flat laid-out state.
Figure 4:
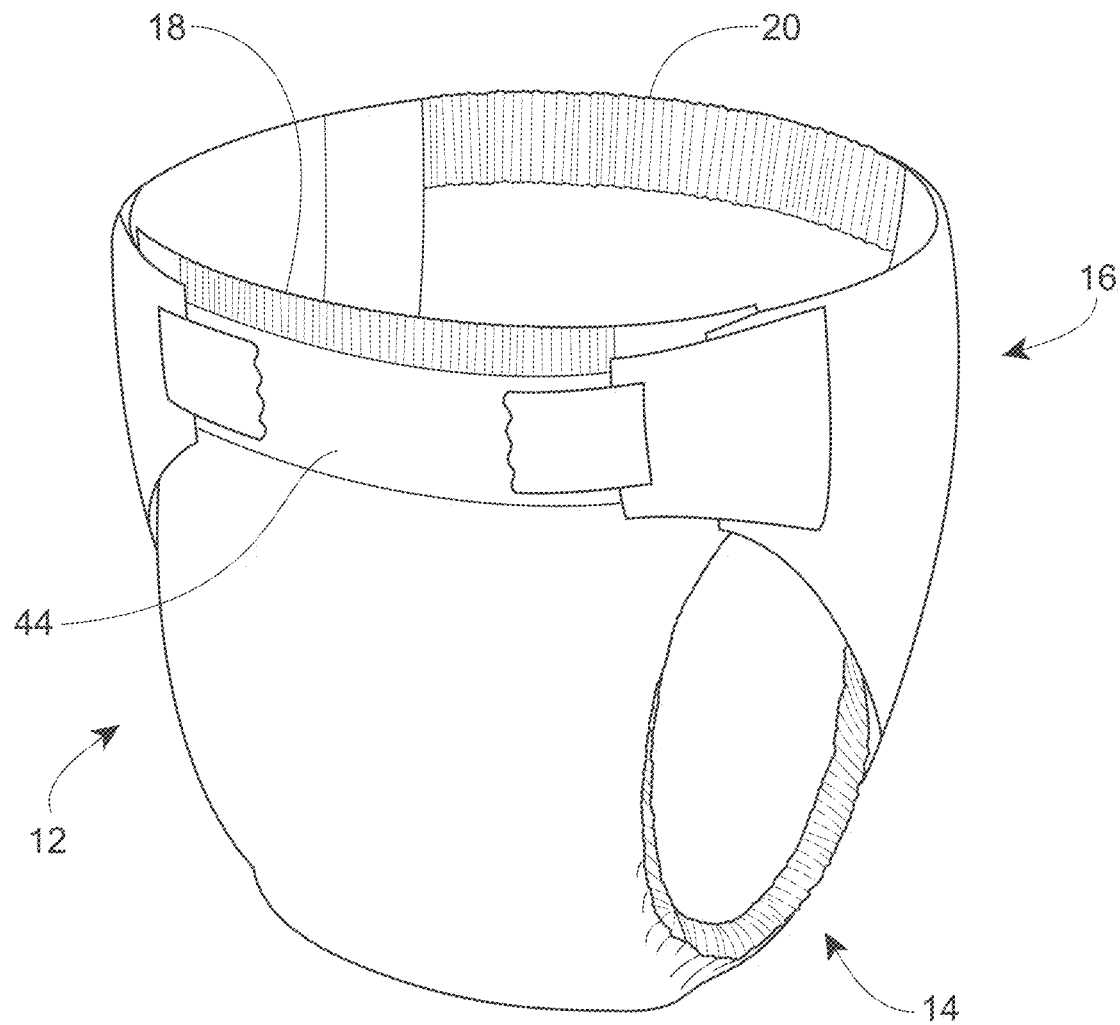
FIG. 4 is a front perspective view of the diaper of FIGS. 2 and 3 in a fastened position.
Figure 5:
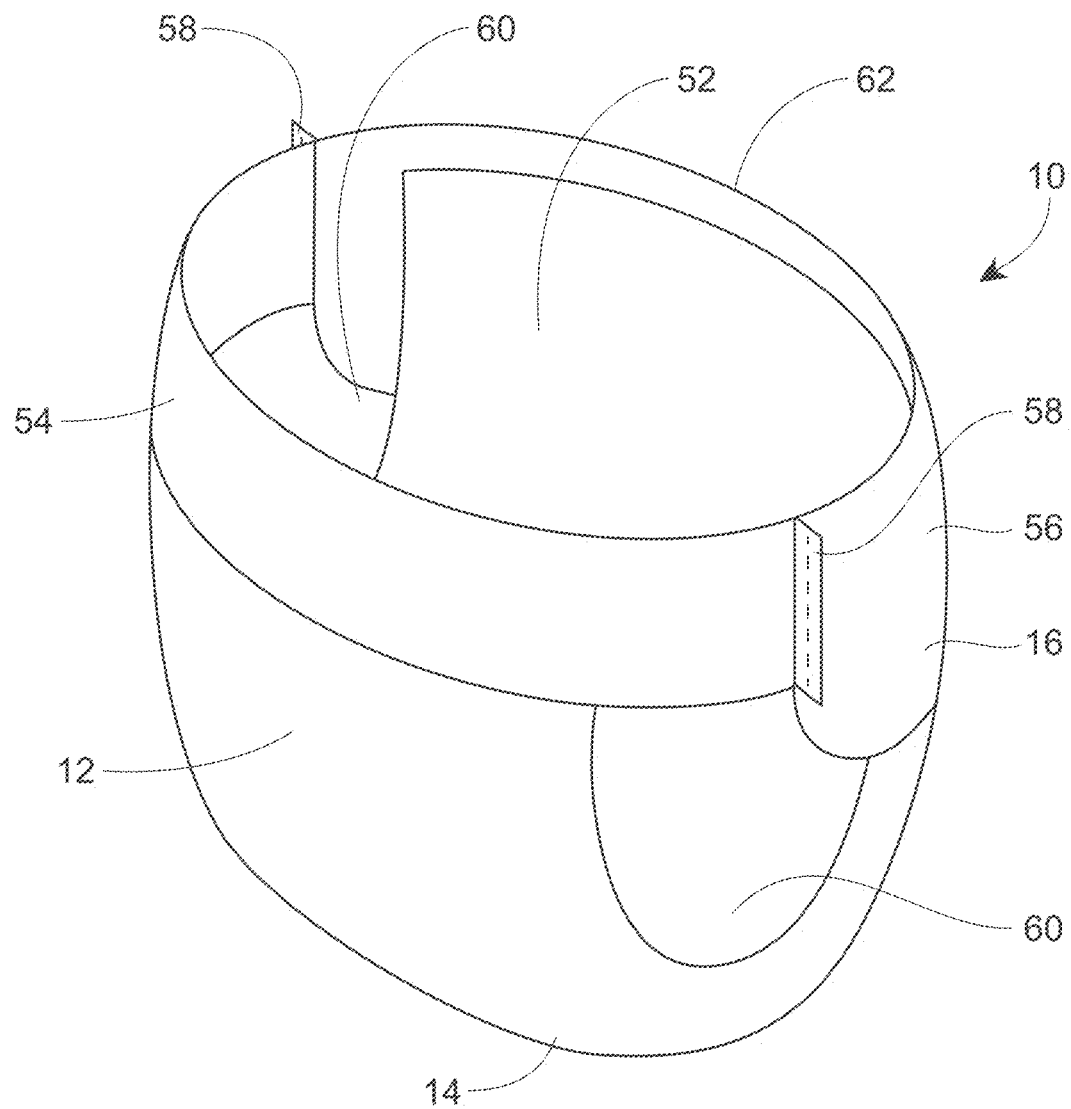
FIG. 5 is a front perspective view of a pant.
Figure 6:
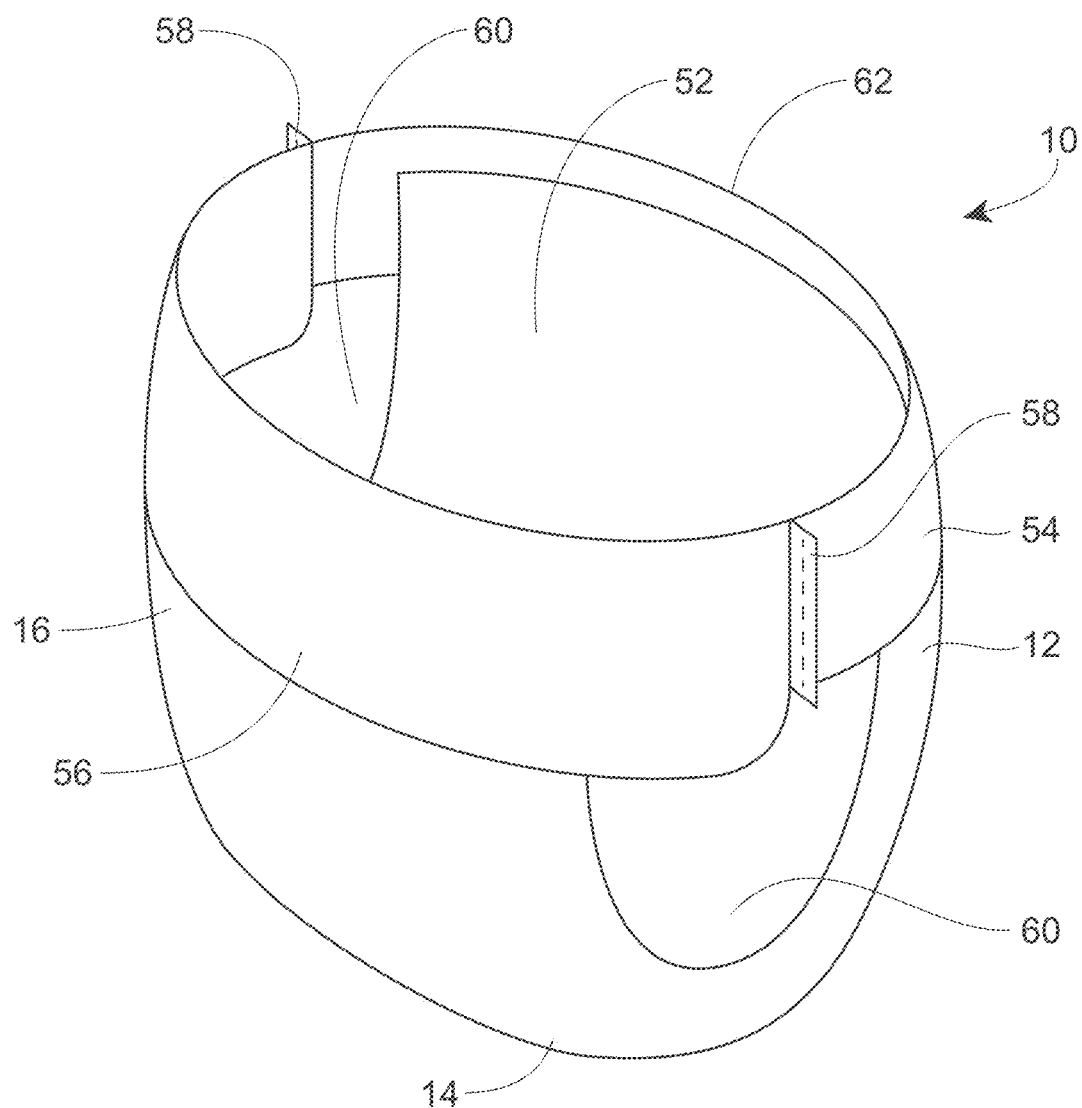
FIG. 6 is a rear perspective view of the pant of FIG. 5.
Figure 11A:
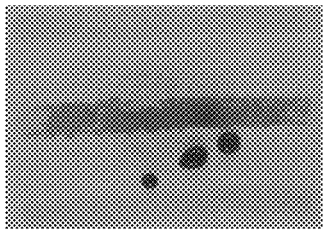
FIG. 11A-D are grayscale images of a Bicomponent topsheet with a GTS additive with and without insult.
Figure 11B:
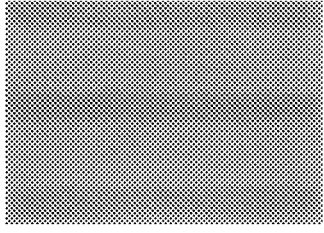
Figure 11C:
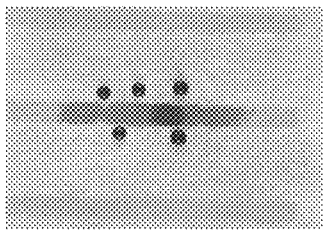
Figure 11D:
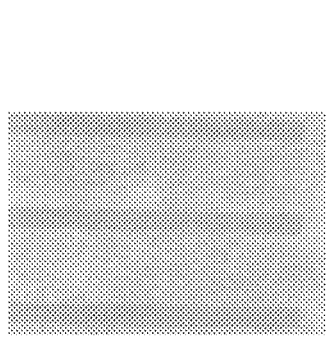
Figure 16B:
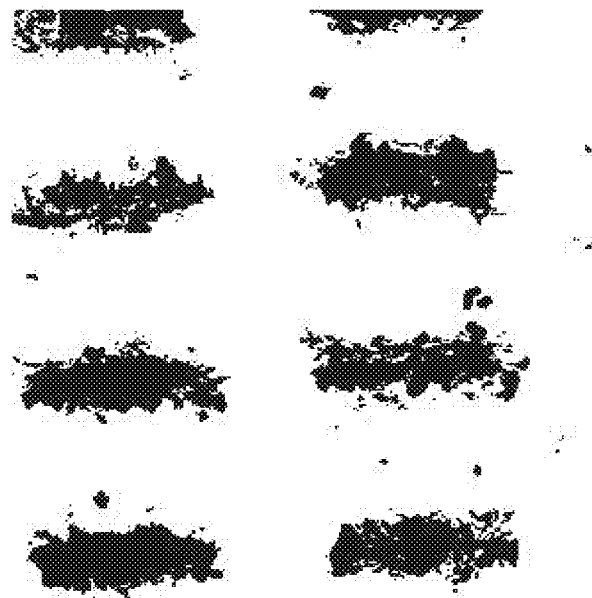
FIG. 16B is an image of a pattern in Binary.
Figure 16A:
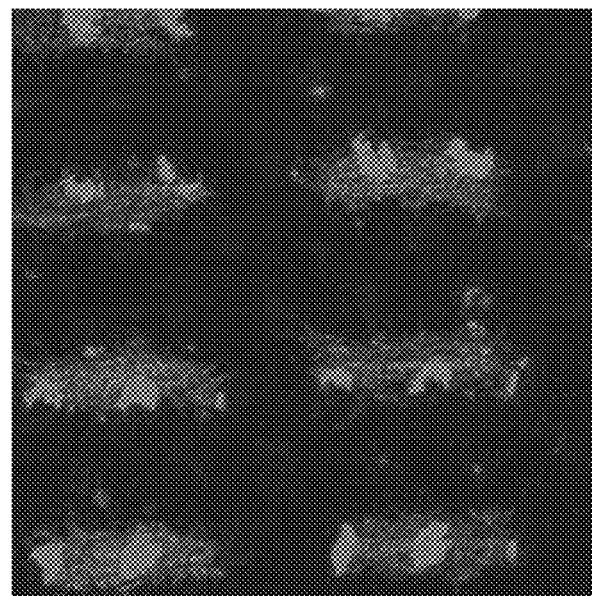
FIG. 16A is an image of a pattern in 8 bit grayscale.
Figure 17A:
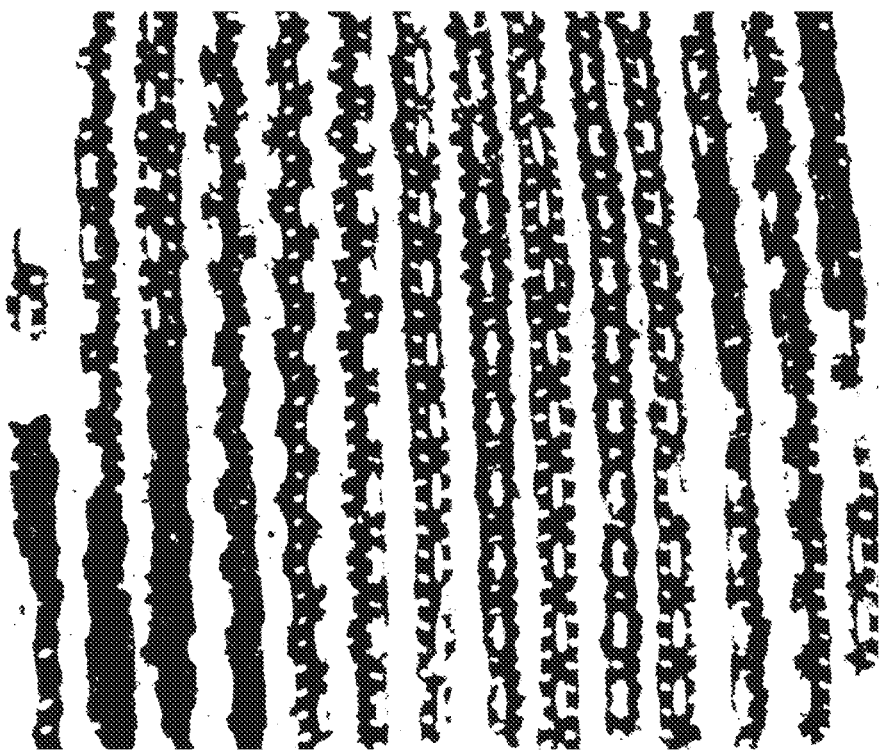
FIG. 17A is an image of a stained pattern in 8 bit grayscale.
Figure 17B:
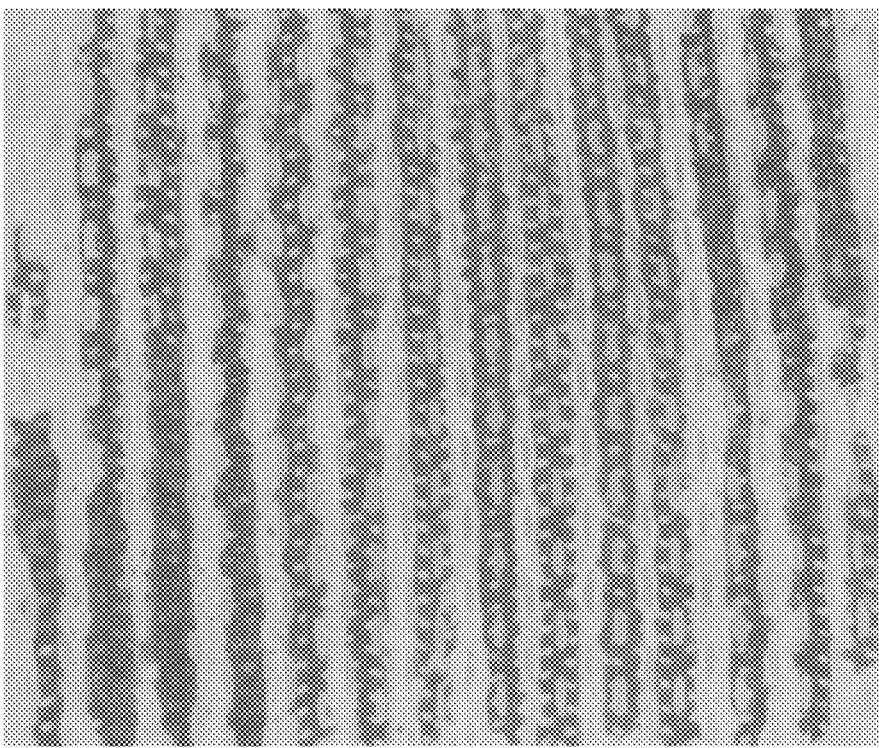
FIG. 17B is an image of a stained pattern in Binary.

An example absorbent article according to the present disclosure, shown in the form of a taped diaper 10, is represented in FIGS. 2-4. FIG. 2 is a plan view of the example diaper, garment-facing surface 2 facing the viewer in a flat laid-out state. FIG. 6 is a plan view of the example diaper of FIG. 2, wearer-facing surface 4 facing the viewer in a flat laid-out state. FIG. 4 is a front perspective view of the diaper of FIGS. 5 and 6 in a fastened position. The diaper of FIGS. 2-4 is shown for illustration purposes only as the present disclosure may be used for making a wide variety of diapers, including adult incontinence products, pants, or other absorbent articles, such as sanitary napkins and absorbent pads, for example.

The absorbent article 10 may include a front waist region 12, a crotch region 14, and a back waist region 16. The crotch region 14 may extend intermediate the front waist region 12 and the back waist region 16. The absorbent article 10 may include a front end edge 18, a back end edge 20 opposite to the front end edge 18, a first side edge 22, and a second side edge 24 opposite to the first side edge 22.

The absorbent article 10 may include a liquid permeable topsheet 26, a liquid impermeable backsheet 28, an absorbent core 30 positioned at least partially intermediate the topsheet 26 and the backsheet 28. The absorbent article 10 may also include one or more pairs of barrier leg cuffs 32, one or more pairs of leg elastics 34, one or more elastic waistbands 36, and/or one or more acquisition materials 38. The acquisition material or materials 38 may be positioned intermediate the topsheet 26 and the absorbent core 30. An outer cover material 40 may cover a garment-facing side of the backsheet 28. The absorbent article 10 may include back ears 42 in the back waist region 16 that may be attached to a landing zone area or landing zone material 44 in the front waist region 12. The back ears 42 may include fasteners 46 and may extend from the back waist region 16 of the absorbent article 10 and attach to the landing zone area or landing zone material 44 on a garment-facing portion of the front waist region 12 of the absorbent article 10, or vice versa. The absorbent article 10 may also have front ears 47 in the front waist region 12. The absorbent article 10 may have a lateral axis 48 and a longitudinal axis 50.

In other instances, the absorbent article may be in the form of a pant having permanent or refastenable side seams. Referring to FIGS. 5-7, an example absorbent article in the form of a pant 10 is illustrated. FIG. 5 is a front perspective view of the pant 10. FIG. 6 is a rear perspective view of the pant 10. FIG. 7 is a plan view of the pant, laid flat, with the garment-facing surface facing the viewer. The pant 10 may have a front waist region 12, a crotch region 14, and a back waist region 16. The pant 10 may has a chassis 52 (sometimes referred to as a central chassis or central panel) including a topsheet 26, a backsheet 28, and an absorbent core 30 disposed intermediate the topsheet 26 and the backsheet 28, and an optional acquisition material 38. The pant 10 may include a front belt portion 54 in the front waist region 12 and a back belt portion 56 in the back waist region 16. The chassis 52 may be joined to a wearer-facing surface of the belt portions 54, 56 or to a garment-facing surface of the belt portions 54, 56. Side areas of the front belt portion 54 may be joined to side areas of the back belt portion 56 to form two seams 58. The seams 58 may be any suitable seams known to those of skill in the art, such as butt seams or overlap seams, for example. When the seams 58 are permanently formed or refastenably closed, the pant 10 has two leg openings 60 and a waist opening circumference 62. The seams 58 may be permanently joined using adhesives or bonds, for example, or may be refastenably closed using hook and loop fasteners, for example. The front belt portion 54 may include a first nonwoven material 64 and a second nonwoven material 66. A plurality of elastic elements 68 (e.g., elastic stands, elastic strips) may be positioned intermediate the first and second nonwoven materials 64, 66. In some instances, an elastic film may be used instead of, or in addition to, the elastic elements 68. The back belt portion 56 may include a first nonwoven material 64 and a second nonwoven material 66. A plurality of elastic elements 68 (e.g., elastic stands, elastic strips) may be positioned intermediate the first and second nonwoven materials 64, 66. In some instances, an elastic film may be used instead of, or in addition to, the elastic elements 68. The elastic elements 68 or film may be relaxed (including being cut) to reduce elastic strain over the core 30 or may alternatively run continuously across the core 30. Elements of FIGS. 5-7 having the same reference number as described above with respect to FIGS. 2-4 may be the same element (e.g., absorbent core 30). FIG. 8 is a cross-sectional view of the front belt portion 54 taken about line 7-7 of FIG. 7. FIG. 9 is a cross-sectional view of the back belt portion 56 taken about line 8-8 of FIG. 7. The elastics elements 68 may have uniform or variable spacing therebetween in any of the belt portions. The elastic elements may also be pre-trained the same amount or different amounts. The first and/or second belt portions 54 and 56 may have one or more elastic element free zones 70 where the chassis 52 overlaps the belt portions 54, 56. In other instances, at least some of the elastic elements 68 may extend across the chassis 52.

The absorbent articles of the present disclosure may be placed into packages. The packages may include polymeric films and/or other materials. Graphics and/or indicia relating to properties of the absorbent articles may be formed on, printed on, positioned on, and/or placed on outer portions of the packages. Each package may include a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Surfactant

The topsheet may have a surfactant. The surfactant can be an individual surfactant or a mixture of surfactants. The surfactant may be a polymeric surfactant or a non-polymeric surfactant. The surfactant may be employed as a wetting agent. The surfactant, when present, may be employed in an amount effective to allow fluid to pass through the topsheet.

The composition may include one or more surfactants. The surfactant or combinations of surfactants may be mild, which means that the surfactants do not overly dry or otherwise harm, damage, or irritate the skin.

A wide variety of surfactants are useful herein and include those selected from the group consisting of anionic surfactants, nonionic surfactants, cationic surfactants, amphoteric surfactants, zwitterionic surfactants, and mixtures thereof.

A wide variety of anionic surfactants may be useful herein. Non-limiting examples of anionic surfactants include those selected from the group consisting of sarcosinates, sulfates, sulfonates, isethionates, taurates, phosphates, lactylates, glutamates, and mixtures thereof. Amongst the isethionates, the alkoyl isethionates may be useful, and amongst the sulfates, the alkyl and alkyl ether sulfates may be useful. Other anionic materials useful herein include soaps (i.e., alkali metal or amine salts, e.g., sodium, potassium or triethanol amine salts) of fatty acids, typically having from about 8 to about 24 carbon atoms.

Nonionic surfactants useful herein include, but are not limited to, those selected from the group consisting of alkyl glucosides, alkyl polyglucosides, polyhydroxy fatty acid amides, alkoxylated fatty acid esters, alkoxylated fatty alcohol ethers, sorbitol esters like sorbitan monostearate, alkoxylated sorbitol esters like polysorbate 60, ethoxylated fatty alcohols like steareth-2 and steareth-20, sucrose esters, amine oxides, and mixtures thereof.

Suitable amphoteric or zwitterionic surfactants for use in the compositions herein include those which are known for use in hair care or other personal care cleansing. Amphoteric surfactants suitable for use in the present compositions are well known in the art and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group such as carboxy, sulfonate, sulfate, phosphate, or phosphonate. Useful amphoteric surfactants include, but are not limited to, the group consisting of cocoamphoacetate, cocoamphodiacetate, lauroamphoacetate, lauroamphodiacetate, and mixtures thereof.

Zwitterionic surfactants suitable for use herein include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Useful zwitterionic detersive surfactants are the betaines, amphoacetates and sulfobetaines, e.g., cocoamidopropylbetaine, sodiumlaurylamphoacetate and cocoamidopropylhydroxysultaine.

Other surfactants that are contemplated herein may include a surfactant or combination of surfactants with hydrophilic/lyophilic balance number (HLB) of greater than or equal to about 7, more desirably greater than or equal to about 10, and even more desirably, a HLB of greater than or equal to about 14. Hydrophilic agents that do not generally have a measured HLB may also be used.

Some suitable examples of hydrophilic compositions include non-ionic surfactants including esters, amides, carboxylic acids, alcohols, ethers-polyoxyethylene, polyoxypropylene, sorbitan, ethoxylated fatty alcohols, alyl phenol polyethoxylates, lecithin, glycerol esters and their ethoxylates, and sugar based surfactants (polysorbates, polyglycosides). Other suitable nonionic surfactants include: ethoxylates, including fatty acid ester ethoxylates, fatty acid ether ethoxylates, and ethoxylated sugar derivatives (e.g., ethoxylated fatty acid polyesters, ethoxylated fatty acid sorbitan esters, and the like), and the like, as well as combinations including at least one of the foregoing. Other suitable examples include anionic surfactants including sulfonates, sulfates, phosphates, alkali metal salts of fatty acids, fatty alcohol monoesters of sulfuric acid, linear alkyl benzene sulfonates, alkyl diphenyloxide sulfonates, lignin sulfonates, olefin sulfonates, sulfosuccinates, and sulfated ethoxylates of fatty alcohols. Other suitable examples include cationic surfactants including amines (primary, secondary, tertiary), quaternary ammoniums, pyridinium, quaternary ammonium salts—QUATS, alkylated pyridinium salts, alkyl primary, secondary, tertiary amines, and alkanolamides. Other suitable examples include zwiterionic surfactants including amino acids and derivatives, amine oxide, betaines, and alkyl amine oxides. Other suitable examples include polymeric surfactants including polyamines, carboxylic acid polymers and copolymers, EO/PO block copolymers, ethylene oxide polymers and copolymers, and polyvinylpyrrolidone. Other suitable examples include silicone surfactants including dimethyl siloxane polymers with hydrophile. And other suitable examples include perfluorocarboxylic acid salts and fluorosurfactants.

The hydrophilic agents that do not generally have a measured HLB may also be used. Such hydrophilic agents may include, without limitation, diols, such as glycols and polyglycols. Suitable nonionic surfactants include, but are not intended to be limited to, C2-8 diols and polyglycols, and the like. Generally, the diol may be glycols (C2 and C3 diols) and polyglycols. The term "polyglycol" refers to a dihydroxy ether formed by dehydration of two or more glycol molecules. A representative, non-limiting list of useful polyglycols, includes: ethylene glycol, propylene glycol, polyethylene glycols, polypropylene glycols, methoxypolyethylene glycols, polybutylene glycols, block copolymers of butylene oxide and ethylene oxide, and the like, as well as combinations including at least one of the foregoing.

Additionally, suitable philic composition include finishing treatments which are typically proprietary blends of synthetic surfactant solutions which are commercially available. Examples include materials from Schill & Seilacher AG under the trade name SILASTOL (e.g. Silastol PHP 26, Silastol PHP 90, Silastol PST-N, Silastol PHP 207, Silastol PHP 28 & Silastol PHP 8), from Pulcra Chemicals under the trade name STANTEX (e.g. Stantex S 6327; Stantex S 6087-4, and Stantex PP 602), among others.

Topsheet Properties

The topsheet may be made to have or imparted with hydrophobic properties. It has been surprisingly found that the by changing the hydrophilic/hydrophobic properties of the topsheet, one can reduce migration of the surfactant used for both the dry and wet state. The hydrophilic/hydrophobic properties may be modified using hydrophobic melt additive, such as, for example GTS, or may be modified using surface treatments. Said otherwise, it has been surprisingly found that by increasing the hydrophobicity of a topsheet, one can reduce the migration of hydrophilic surfactants placed on the areas with increased hydrophobicity. The increased hydrophobic areas may be treated with a surface treatment, such as, for example, a melt additive, to increase the hydrophobic level of the topsheet. The treatment may be placed evenly over the surface of the topsheet or limited to portions of the topsheet. The treatment may be incorporated into the fibers of the topsheet prior to the manufacturing of the topsheet. Without being bound by theory, it is believed that the reduced migration of surfactant is caused by interactions between the hydrophobic treatment and the surfactant hydrophobic tail, thereby locking the surfactant in place.

Surface Treatments

The topsheet may be rendered hydrophobic by the use of a treatment. Suitable treatments include petroleum-based hydrocarbons having from about 4 to about 32 carbon atoms, fatty alcohols having from about 12 to about 24 carbon atoms, polysiloxane compounds, fatty acid esters, alkyl ethoxylates, fatty alcohol ethers having from about 12 to about 28 carbon atoms in their fatty chain, lanolin and its derivatives, glyceride derivatives including acetoglycerides and ethoxylated glycerides of C12-C28 fatty acids, and mixtures thereof. Alternatively or in combination with, the treatment may also be composed of polysiloxane compounds non-limiting examples include dimethicones (1-100,000,000 centistoke), cyclomethicones, alkylated silicones (hair conditioning agents), amino functional silicones, silicone gums, silicone gels, silicone waxes, copolymers of silicone (vinyl dimethicone polymers, phenyl vinyl dimethicone polymers, alkylated silicone polymers, polyethylene oxide/silicone copolymers, polyethylene oxide/alkyl silicone copolymers), and mixtures thereof.

Nonlimiting examples of suitable petroleum-based hydrocarbons having from about 4 to about 32 carbon atoms include mineral oil, petrolatum, isoparaffins, various other branched chained hydrocarbons, and combinations thereof. Mineral oil is also known as "liquid petrolatum", and usually refers to less viscous mixtures of hydrocarbons having from about 16 to about 20 carbon atoms. Petrolatum is also known as "mineral wax", "petroleum jelly", and "mineral jelly", and usually refers to more viscous mixtures of hydrocarbons having from about 16 to about 32 carbon atoms. An example of commercially available petrolatum include petrolatum sold as PROTOPET 1S, obtained from the Witco Corporation, Greenwich, Conn.

Nonlimiting examples of suitable fatty alcohols having from about 12 to about 24 carbon atoms include saturated, unsubstituted, monohydric alcohols or combinations thereof, which have a melting point less than about 110° C., preferably from about 45° C. to about 110° C. Specific examples of fatty alcohol include, but are not limited to, cetyl alcohol, stearyl alcohol, cetearyl alcohol, behenyl alcohol, arachidyl alcohol, lignocaryl alcohol, and combinations thereof Examples of commercially available cetearyl alcohol is STENLO 1822 and behenyl alcohol is LANETTE 22, both of which are available from the Cognis Corporation, Cincinnati, Ohio.

Nonlimiting examples of suitable fatty acid esters include those fatty acid esters derived from a mixture of $C_{12}$-$C_{28}$ fatty acids and short chain ($C_1$-$C_8$, preferably $C_1$-$C_3$) monohydric alcohols preferably from a mixture of $C_8$-$C_{30}$ saturated fatty acids and short chain ($C_1$-$C_8$, preferably $C_1$-$C_3$) monohydric alcohols. Representative examples of such esters include methyl palmitate, methyl stearate, isopropyl laurate, isopropyl myristate, isopropyl palmitate, ethylhexyl palmitate, and mixtures thereof. Suitable examples of triglycerides include glycerol thibehenate (C22), glycerol tristearate (C18), glycerol tripalmitate (C16), and glycerol trimyristate (C14), and mixtures thereof. In the case of triglycerides and diglycerides, the alkyl chains could be the same length, or different length. Example includes a triglyceride with one alkyl C18 chain and two C16 alkyl chain, or two C18 alkyl chains and one C16 chain. Preferred triglycerides include alkyl chains derived from C14-C22 fatty acids. Suitable fatty acid esters can also be derived from esters of longer chain fatty alcohols ($C_8$-$C_{28}$, preferably $C_8$-$C_{16}$) and shorter chain fatty acids such as lactic acid, specific examples of which include lauryl lactate and cetyl lactate.

Nonlimiting examples of suitable alkyl ethoxylates include $C_8$-$C_{22}$ fatty alcohol ethoxylates having an average degree of ethoxylation of from about 2 to about 30. A more detailed description of carrier ingredients including suitable hydrocarbons, polysiloxane compounds, and fatty alcohol ethoxylates can be found in U.S. Pat. No. 5,643,588, issued Jul. 1, 1997 to Roe et al. entitled "Diaper Having A Lotioned Topsheet".

Some suitable examples of hydrophobic compositions include fluorinated or perfluorinated polymers; silicones; fluorochemicals; zirconium compounds; oils; latexes; waxes; crosslinking resins; and blends thereof; fluorochemical urethanes, ureas, esters, ethers, alcohols, epoxides, allophanates, amides, carbodiimides, guanidines, oxazolidinones, isocyanurates, and biurets; nanostructured particles selected from fumed silica, hydrophobic titania, zinc oxide, nanoclay, and mixtures thereof; fats and oils, glycerol derivatives; hydrophobic silicones or suitable combinations thereof.

Examples of suitable silicone polymers are selected from the group consisting of silicone MQ resins, polydimethysiloxanes, crosslinked silicones, silicone liquid elastomers, and combinations thereof. Polydimethylsiloxanes can be selected from the group consisting of vinyl-terminated polydimethsiloxanes, methyl hydrogen dimethylsiloxanes, hydroxyl-terminated polydimethysiloxanes, organo-modified polydimethysiloxanes, and combinations thereof, among others.

Other hydrophobic materials suitable for the present invention are well defined and documented in the art. For example, US 2002/0064639 describes hydrophobic compositions selected from the group consisting of silicones, fluorochemicals, zirconium compounds, oils, latexes, waxes, crosslinking resins, and blends thereof. Representative water repellent fluorochemical compounds described in U.S. Pat. No. 7,407,899 include fluorochemical urethanes, ureas, esters, ethers, alcohols, epoxides, allophanates, amides, amines (and salts thereof), acids (and salts thereof), carbodiimides, guanidines, oxazolidinones, isocyanurates, and biurets. U.S. Pat. No. 6,548,732 describes hydrophobic substances from the group consisting of *theobroma* oil, cacao butter, cocoa butter, petrolatum, mineral jelly, white mineral oil, dimethicone, zinc oxide preparation, chinese white, zinc white, beeswax, lanolin, jojoba oil and combinations thereof. Additionally, U.S. application Ser. No. 13/193,065, filed Jul. 28, 2011 discusses substrates that exhibit superhydrophobic properties when treated with a composition including a hydrophobic component selected from fluorinated polymers, perfluorinated polymers, and mixtures thereof nano-structured particles selected from fumed silica, hydrophobic titanic, zinc oxide, nanoclay, and mixtures thereof and water for an overall water-based, non-organic solvent. Examples of such compositions and surfaces in U.S. application Ser. No. 13/193,065, filed Jul. 28, 2011 exemplify the superhydrophobic treated surfaces that may be used as the nonwoven topsheet of the present invention.

Additionally waxes and other hydrophobic materials can be used, including petroleum-based emollients; fatty acid esters; polyol polyesters; fatty alcohol ethers; sterols and sterol esters, and their derivatives; triglycerides; glyceryl esters; ceramides; and mixtures thereof. The fatty acids may originate from vegetable, animal, and/or synthetic sources. Some fatty acids may range from a C8 fatty acid to a C30 fatty acid, or from a C12 fatty acid to a C22 fatty acid. In another embodiment, a substantially saturated fatty acid may be used, particularly when saturation arises as a result of hydrogenation of fatty acid precursor. Examples of fatty acid derivatives include fatty alcohols, fatty acid esters, and fatty acid amides.

Suitable fatty acid amides include those derives from a mixture of C12-C28 fatty acids (saturated or unsaturated) and primary or secondary amines. A suitable example of a primary fatty acid amide includes those derived from a fatty acid and ammonia.

Other suitable examples include erucamide, oleamide and behanamide.

Other suitable hydrophobic actives include oils or fats, such as natural oils or fats, or natural oil or fat derivatives, in particular of plant or animal origin. Suitable carriers further encompass waxes. As used herein, the term 'wax' refers to oil soluble materials that have a waxy constituency and have a melting point or range of above ambient temperature, in particular above 25° C. Waxes are materials that have a solid to semi-solid (creamy) consistency, crystalline or not, being of relative low viscosity a little above their liquefying point. Suitable waxes which can be incorporated into the lotion composition include animal, vegetable, mineral or silicone based waxes which may be natural or synthetic, and including mixtures thereof.

Melt Additives

Examples of hydrophobic melt additives include fatty acids and fatty acid derivatives. The fatty acids may originate from vegetable, animal, and/or synthetic sources. Some fatty acids may range from a C8 fatty acid to a C30 fatty acid, or from a C12 fatty acid to a C22 fatty acid. In other forms, a substantially saturated fatty acid may be used, particularly when saturation arises as a result of hydrogenation of fatty acid precursor. Examples of fatty acid derivatives include fatty alcohols, fatty acid esters, and fatty acid amides.

Suitable fatty alcohols (R—OH) include those derived from C12-C28 fatty acids, such as R—OH R=C12-C28 alkyl chain Suitable fatty acid esters include those fatty acid esters derived from a mixture of C12-C28 fatty acids and short chain (C1-C8, preferably C1-C3) monohydric alcohols preferably from a mixture of C12-C22 saturated fatty acids and short chain (C1-C8, preferably C1-C3) monohydric alcohols. The hydrophobic melt additive may include a mixture of mono, di, and/or tri-fatty acid esters. An example includes fatty acid ester with glycerol as the backbone:

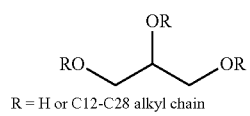

R = H or C12-C28 alkyl chain

The glycerol derived fatty acid ester has at least one alkyl chain, at least two, or three chains to a glycerol, to form a mono, di, or triglyceride. Suitable examples of triglycerides include glycerol thibehenate (C22), glycerol tristearate (C18), glycerol tripalmitate (C16), and glycerol trimyristate (C14), and mixtures thereof. In the case of triglycerides and diglycerides, the alkyl chains could be the same length, or different length. Example includes a triglyceride with one alkyl C18 chain and two C16 alkyl chain, or two C18 alkyl chains and one C16 chain. Preferred triglycerides include alkyl chains derived from C14-C22 fatty acids.

Suitable fatty acid amides include those derives from a mixture of C12-C28 fatty acids (saturated or unsaturated) and primary or secondary amines. A suitable example of a primary fatty acid amide includes those derived from a fatty acid and ammonia:

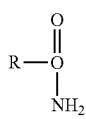

R = C12-C28 alkyl chain

Other suitable examples include erucamide, oleamide and behanamide.

Other suitable hydrophobic melt additives include hydrophobic silicones, ethoxylated fatty alcohols. Additional suitable hydrophobic melt additives are disclosed in U.S. application Ser. No. 14/849,630 and U.S. application Ser. No. 14/933,028. One specific example of a melt additive is glycerol tristearate (GTS). As used herein, GTS is defined as a mixture of long-chained triglycerides containing predominately C18 and C16 saturated alkyl chain lengths.

One objective for deposition of a surfactant in a precise location is that it does not migrate once applied. Without being bound by theory, it has been surprisingly found that the key factor that reduces migration is the properties of the web in which the surfactant is printed. For example, as shown in the tables below, the addition of a hydrophobic chemistry on the web which can interact with the surfactant can rendered it immobile. This is exemplified below using STANTEX S 6327 surfactant in combination with different hydrophobic treatments. STANTEX S 6327, from Pulcra Chemicals LLC, Rock Hill, S.C. (affiliate of Fashion Chemicals GmbH & Co. KG, Geretsried, Germany), is a blend of fatty acid esters.

As shown in the table, the migration of surfactants may be impacted by the coating on the nonwoven web. For example, as shown below, the migration of surfactant on one of either a bicomponent (BICO) or a polypropylene nonwoven web may be impacted by first placing a hydrophobic additive or treatment on the web. Bicomponent is defined as a fiber having two separate parts in a spatial relationship to one another. The different components of multicomponent fibers such as bicomponent fibers are arranged in substantially distinct regions across the cross-section of the fiber and extend continuously along the length of the fiber.

TABLE 1

| Wet & Dry Migration on topsheets with various treatments treated with nonionic surfactant | | | |
|---|---|---|---|
| FIBER | Fresh Wet ($M_{wet\,1}$) | Dry 1M ($M_{dry}$) | Aged Wet ($M_{wet\,A}$) |
| BiCo | | | |
| BiCo | 2.5 | 1.5 | 3.5 |
| BiCo + GTS | 1.1 | 1.3 | 1.4 |
| Bico + WR1300 | 1.3 | 1.1 | 1.2 |
| Bico + AEROSIL ® R 812 | 1.4 | 1.5 | 2.6 |
| POLYPROPYLENE | | | |
| PP | 2.8 | 1 | 2.6 |
| PP + Erucamide | 1.2 | 1 | 1.3 |

As shown in Table 1 above, the use of Glycerol Tristearate (GTS) MA, Erucamide MA, silica hydrophobic modified particles (AEROSIL® R 812), and hydrophobic silicone (WR1300, a functional silicone fluid sold by Wacker Chemie AG) each impacted the migration of surfactant placed on the web for both dry migration and wet migration. Dry migration is the movement of the surfactant from the application spot with ageing. Wet migration is the movement of fluid to regions beyond the location of the surfactant. In the samples above, the surfactant (STANTEX® S 6327) was printed in 5 mm by 80 mm stripes at a 3 gsm basis weight. The webs were aged at 40 C/75% Relative Humidity for 1 month.

In this context, dry migration refers to the surfactant migrating from the initial location during ageing. Wet migration refers, to how much the fluid wets the hydrophobic portions of the web after been in contact with the surfactant. In a sense, wet migration can be attributed to either surfactant movement when dry or wet, or an increase in fluid movement due to a reduction in the fluid surface tension when in contact with the surfactant.

As shown in the table above, GTS and WR1300 significantly improved surfactant migration versus AEROSIL® R 812 (AEROSIL® R 812 S distributed by Evonik). Without being bound by theory, it is believed that the AEROSIL® R 812 hydrophobic particles are not able to bind to the fibers thereby not having the same effect as GTS and WR1300. However, it is important to note that, when compared to BiCo alone, the AEROSIL R 812 treatment reduced migration upon being wetted in both the Fresh Wet and Aged Wet samples.

Without intending to be bound by theory, it has been found that treating a topsheet with a hydrophobic material having an alkane chain of at least $C_{12}$ to $C_{22}$ hydrocarbons is capable of interacting with a nonionic surfactant in a manner that binds up the nonionic surfactant. It is believed that this may occur when the nonionic surfactant includes a PEG diester having a carbon chain of $C_{12}$ or greater; when the nonionic surfactant includes a $C_{12}$ or greater alcohol ethoxylates or PEG diesters; when the nonionic surfactant includes a PEG group that is at least 5 ethylene oxide units, such as, for example 6 ethylene oxide groups, or greater than 10 ethylene oxide groups; when the nonionic surfactant includes a blend having greater than 50% $C_{12}$ or greater chain length; or when the nonionic surfactant includes an ethoxylated derivative containing a hydroxyl acid alkyl chain.

Additionally and without intending to be bound by theory, it has been found that both the level of surfactant and the amount of hydrophobic used to make the hydrophobic treated web hydrophilic should meet certain criteria for the benefit to be derived. Specifically, a hydrophobic web may be treated with greater than 0.5 gsm treatment (local printed or local patterned) in order to make the hydrophobic treated web philic at the printed zone. On a non-hydrophobically treated web, one requires less surfactant to make the topsheet hydrophilic. However, when using less treatment, it has been found that surfactant migration increases when the sample is wet.

Without intending to be bound by theory, it has been found that by correlating the level of surfactant added to an amount of hydrophobicity of the surface on which the surfactant is placed, one can minimize surfactant migration. The appropriate level of hydrophobicity may be achieved by adding a hydrophobic treatment. Hence, once the amount of surfactant desired is quantified, one can calculate the required level of hydrophobicity desired to reduce surfactant migration or vice versa, based on the level of hydrophobicity of the web one can quantify the required amount of surfactant needed to rendered it philic. The required level of hydrophobicity may then be achieved by calculating the amount of hydrophobic treatment needed to be added to a topsheet that achieves the desired hydrophobicity of the topsheet with the hydrophobic treatment. As such, without being bound by theory, for any given topsheet, one can calculate the level of hydrophobic treatment needed to reduce surfactant migration for a given level of surfactant.

As stated above, the level of surfactant is applied impacts surfactant migration. As the level of surfactant increases, the amount of migration, with all other variables held constant, will increase. However, when the web is treated with greater than 0.5 gsm of additive and the surfactant is between 0.5 gsm and 3 gsm, the treated area behaves hydrophilic and exhibits a wet migration of less than 2. It is believed that at greater than 3 gsm, the surfactant will spread when dry or wet due to the high level of surfactant. This is unlike most webs currently in market that utilize between 0.1 gsm and 0.16 gsm of surfactant or 0.4% to 0.65%. Further, when the treatment is used at greater than 0.5 gsm and the surfactant is between 0.5 gsm and 3 gsm, the material exhibits a strikethrough of less than 5 seconds. Strikethrough is recognized as the amount of time needed for a set given quantity of fluid to be absorbed from the upper surface into the absorbent layer.

Figures Illustrating Table Data

FIGS. 10-15 represent the articles from the table above. As shown in FIGS. 10-15, FIG. A represents the fresh dry sample, FIG. B represents the fresh wet sample, FIG. C represents the dry sample after 1 month at 40 Celsius and 75% relative humidity, and FIG. D represents the wet sample after 1 month at 40 Celsius and 75% relative humidity.

FIGS. 10A-D (shown in grayscale) represent the bico samples without an additive. FIGS. 11A-D represents the BICO+GTS samples. FIGS. 12A-D represent the Bico samples with WR1300. FIGS. 13A-D represent the bico Samples with AEROSIL R 812. FIGS. 14A-D represent the Polypropylene samples without an additive. FIG. 15A-D represent the polypropylene samples with erucamide.

As stated above, dry migration was simply measured as the change in the printing pattern. For wet migration, drops of saline with a blue dye were added. Fluid spreading was measured for the drops of saline with a blue dye. Samples were tested one day after printing and after 1 month in aging.

As shown above in Table 1 and in FIGS. 10-15, dry migration was worst on BiCo substrates compared to the PP substrate. This is better observed in the images of the webs. However, both untreated substrates (BiCo and PP) lead to significant wet migration. Additionally BiCo with the AEROSIL® R 812 particles also had wet migration (greater than 2). However, when compared to untreated BiCo, the AEROSIL® R 812 particles did reduce overall surfactant migration. It is believed that the AEROSIL® R 812 particles are not capable of binding the surfactant to the web surface as effectively as a non-particled treatment.

The hydrophobic treatments with GTS, erucamide and WR1300, all reduced wet migration keeping only the zones with surfactant hydrophilic. Some dry migration is visible with GTS but the fluid stayed localized in the zones with surfactant. Without being bound by theory, there appears to be a different mechanism for surfactant migration dry vs retention wet. Because there are no binders immobilizing the surfactant, it is believed that the interaction of the surfactant with the web is important. It is believed that the hydrophobe of the surfactant interacts with the alkyl chains of the hydrophobic treatment molecules "binding" it to the surface.

The surfactant may be added by ink jet printing from a solution in ethanol. In addition to ink jet, several contact methods can be used to apply a surfactant formulation onto a web. Other methods may be used to add the surfactant formulation to the web including flexographic printing, spray, slot coating, etc. Surfactant can also be added online at high speeds provided that the surfactant is liquid at 70 degrees Celsius or greater and stable at high temperature and may be applied pure. For example, Stantex S6327 may be added under these conditions with the use of solvents by printing.

As shown in the tables below, one can modify printing patterns and the composition of the melt additive used on the fibers. For example, one may vary the separation between surfactant stripes and the dimensions of the surfactant strips (both width and length).

Compositions disclosed herein can be applied by printing methods, or continuous spray or extrusion as is known in the art, or as is disclosed in U.S. Pat. No. 5,968,025 or methods described in U.S. application Ser. No. 62/385,265 filed on Sep. 9, 2016.

The composition of the present invention may be formulated to optimize its deposition by non-contact printing, e.g. ink jet printing. For example, the components of the desired composition can be dissolved or dispersed in a suitable solvent, such as water or another organic solvent. Some suitable organic solvents include ketones such as acetone, diethyl ketone, cyclohexanone and the like. Additional suitable solvents include alcohols such as methanol, ethanol, n-propanol, isopropanol, n-butanol, 1-methoxy-2-propanol, and the like. Additional suitable solvents include esters such as ethyl acetate, propyl acetate, butyl acetate and the like. Additional examples include ethers, lactones and amides. If desired, a mixture of solvents may be used. Additionally surfactants, rheology modifiers, and colorants such as dyes or pigments may be added to the formulation.

Additional forms are contemplated where the compositions to be deposited can be heated such that the viscosity of the composition is provided in the correct range for deposition via ink jet. For example, heated print heads for hot melts are available from Fujifilm Dimatix, Inc., Santa Clara, Calif. under the trade name GALAXY PH256/80HM.

Inkjet printing generally relies on the generation of sequences of droplets. Behavior of the composition during droplet ejection is dependent on material properties such as density, viscosity and surface tension. The behavior of a composition when inkjet printed can be predicted via two dimensionless numbers, i.e. Ohnesorge number and Weber number. The equation for determining the Oh number is:

$$Oh = \frac{\eta}{\sqrt{\rho \gamma L}}$$

where $\eta$ is viscosity, $\rho$ is density, $\gamma$ is surface tension of the composition, and L is the characteristic diameter (print head nozzle diameter for inkjet printing in meters).

Stable drop formation can be characterized by the reciprocal of the Ohnesorge number, namely Z=1/Oh. Stable drop formation can be expected from compositions when 14≥Z≥1. The viscosity of the desired composition should be measured at target operating temperature with shear rates between 200 and 20 s−1. The surface tension should be recorded in N/m. The density should be calculated in kg/m3, and the viscosity should be recorded in Pa·s.

Additionally, a composition of the present invention may include a Weber number of between about 4 and 1000. The Weber number may be calculated as follows:

$$We = \frac{v^2 \rho L}{\gamma}$$

where $\rho$ is the density of the composition in kg/m3; v is the velocity of the composition in m/s; L is the characteristic diameter (print head nozzle diameter for inkjet printing; and $\gamma$ is the surface tension in N/m.

The compositions of the present invention may include a viscosity of between about 5 and 25 centipoise. The compositions may include a surface tension of between about 25 and 40 dyne. In some forms of the present invention, the compositions may include a density of from about 0.6 grams/cubic cm to about 2.0 grams/cubic cm, specifically including all values within this range and any ranges created thereby.

Any suitable printer may be utilized for purposes of the present invention. As noted previously, the composition sites may include a plurality of discrete dots or droplets. The volume of the ink droplets can depend on the particular printing technology. By way of example, printing units that are VIDEOJET continuous ink jet printers can have ink drop volumes of about 240 pL and are delivered at relatively high drop velocities (e.g., about 13 m/s). Other printing technology (e.g. piezo drop on demand) can deliver ink drops having relatively small volumes, such as ink drops having a volume ranging from about 1 pL to about 80 pL, that are delivered at lower drop velocities (i.e., about ½ m/s) than continuous inkjet printing. Those skilled in the art know there are different inkjet technologies (e.g., continuous, piezo, thermal, valve) and different drop size ranges and different jet velocities. In general, smaller drop size infers that the CD dpi (resolution) is higher. The range 1-24 pL would equate to a CD resolution of 300-600 dpi. The VIDEOJET CD resolution is 128 dpi. So, more drops in CD can mean better opportunity to hit a fiber, which can result in better image quality and less ink blow-though. The slower the drop speed, the less ink blow-through.

An exemplary continuous ink jet printer is available from Videojet Technologies, Inc., Wood Dale, Ill., sold under the trade name VIDEOJET BX. For the continuous ink jet printer, the ink droplets are dispensed from all of the jets of the print heads continuously, but only certain ink droplets are allowed to reach the precursor web, intermediate web, or secondary web, at the composition sites. The other ink droplets can be prevented from reaching the precursor web, intermediate web, or secondary web by deflecting the ink droplets into a recycling flow for a continuous re-use. The operation of the individual ink jets of each print head can be controlled by a controller included in the VIDEOJET BX system.

Exemplary drop on demand printers for use in the present invention may include multiple print heads allowing for the deposition of a plurality of compositions. In general, the printer of the present invention may include a controller, one or more print heads, and a composition management system. A suitable example of a printer includes the 1024 PH development kit available from FujiFilm Dimatix, Inc., Santa Clara, Calif. A suitable example of the print heads which may be utilized, includes SG-1024 MA available from FujiFilm Dimatix, Inc.

Examples Contemplated by the Present Disclosure

A. An absorbent article including: a liquid pervious topsheet, said topsheet having an inner surface oriented toward the interior of said absorbent article and an outer surface oriented toward the skin of the wearer when said absorbent article is being worn wherein at least a portion of the topsheet has been treated to be hydrophobic, a backsheet joined to said topsheet, said backsheet having an inner surface oriented toward the interior of said absorbent article and an outer surface oriented toward the garment of the wearer when said absorbent article is being worn;

an absorbent core disposed between said topsheet and said backsheet, said absorbent core having an inner surface oriented toward the skin of the wearer when said absorbent article is being worn and an outer surface oriented toward the garment of the wearer when said absorbent article is being worn;

and a surfactant applied to at least a portion of said outer surface of said topsheet wherein the topsheet has been treated hydrophobic and wherein the hydrophilic surfactant is added to the areas treated hydrophobic.

B. The absorbent article of example A, wherein the topsheet includes hydrophobic and hydrophilic zones, wherein the hydrophilic zones include hydrophilic surfactant placed on areas having hydrophobic treatments.

C. The absorbent article of examples A-B, wherein the Surfactant is nonionic, cationic, anionic or combinations thereof.

D. The absorbent article of examples A-C, wherein the surfactant includes a PEG diester having a carbon chain of $C_{12}$ or greater.

E. The absorbent article of examples A-D, wherein the surfactant includes a $C_{12}$ or greater alcohol ethoxylates or PEG diesters.

F. The absorbent article of examples A-E, wherein the surfactant includes a PEG group that is at least 5 ethylene oxide units.

G. The absorbent article of example F, wherein the surfactant includes a PEG group that is between 6 ethylene oxide groups and 20 ethylene oxide groups.

H. The absorbent article of examples A-G, wherein the surfactant includes a blend having greater than 50% $C_{12}$ or greater chain length.

I. The absorbent article of examples A-H, wherein the surfactant includes an ethoxylated derivative containing a hydroxyl acid alkyl chain.

J. The absorbent article of examples A-I, wherein the topsheet is treated hydrophobic by a treatment selected from the group consisting of petroleum-based hydrocarbons having from about 4 to about 32 carbon atoms, fatty alcohols having from about 12 to about 24 carbon atoms, polysiloxane compounds, fatty acid esters, alkyl ethoxylates, fatty alcohol ethers having from about 12 to about 28 carbon atoms in their fatty chain, lanolin and its derivatives, glyceride derivatives including acetoglycerides and ethoxylated glycerides of C12-C28 fatty acids, fatty amides, and combinations thereof.

K. The absorbent article of examples A-J, wherein the topsheet is treated hydrophobic by a treatment selected from the group consisting of amides, tryglicerides, functional silicones, WR1300, or combinations thereof.

AA. A method of limiting surfactant migration on a topsheet, the method including:
providing a nonwoven including a hydrophobic coating treatment or including a hydrophobic melt additive; and treating the portions of the topsheet treated with the hydrophobic coating treatment or the hydrophobic melt additive with a surfactant.

BB. The method of example AA, wherein the surfactant includes a PEG diester having a carbon chain of $C_{12}$ or greater;

CC. The method of examples AA-BB, wherein the surfactant includes a $C_{12}$ or greater alcohol ethoxylates or PEG diesters;

DD. The method of examples AA-C, wherein the surfactant includes a PEG group that is at least 5 ethylene oxide units.

EE. The method of example DD, wherein the surfactant includes a PEG group that is between 6 ethylene oxide groups and 20 ethylene oxide groups.

FF. The method of examples AA-EE, wherein the surfactant includes a blend having greater than 50% $C_{12}$ or greater chain length;

GG. The method of examples AA-FF, wherein the surfactant includes an ethoxylated derivative containing a hydroxyl acid alkyl chain.

HH. The method of examples AA-GG, wherein the topsheet is treated hydrophobic by a treatment selected from the group consisting of petroleum-based hydrocarbons having from about 4 to about 32 carbon atoms, fatty alcohols having from about 12 to about 24 carbon atoms, polysiloxane compounds, fatty acid esters, alkyl ethoxylates, fatty alcohol ethers having from about 12 to about 28 carbon atoms in their fatty chain, lanolin and its derivatives, glyceride derivatives including acetoglycerides and ethoxylated glycerides of C12-C28 fatty acids, combinations thereof.

II. The method of examples AA-HH, wherein the topsheet is treated hydrophobic by a treatment selected from the group consisting of Erucamide, GTS, WR1300, or combinations thereof.

Test Methods

Wet and Dry Migration for Raw Materials

A suitable method to demonstrate an effective execution of printing a hydrophilic pattern onto a nonwoven substrate is as follows. Wet and dry migration of the printed hydrophilic pattern are assessed by comparing the initial printed pattern dimensions on a nonwoven substrate to the printed pattern dimensions on the aged nonwoven substrate using image analysis. All measurements are performed at constant temperature (23° C.±2 C.°) and relative humidity (50%±2%).

Various methods can be used to apply a hydrophilic coating pattern to a nonwoven substrate. One suitable way is to use an ink jet printer (e.g. 1024 PH development kit, available from FujiFilm Dimatix, Inc., Santa Clara, Calif., or equivalent). The print DPI (dots per inch) is used to control the amount of hydrophilic coating applied to the nonwoven, and the basis weight of hydrophilic coating add-on is reported as grams per square meter locally printed in the pattern.

The nonwoven sample printed with a hydrophilic coating (printed side facing up), along with a distance scale (e.g. a calibrated ruler traceable to NIST or equivalent) are laid horizontally flat on a matte white background inside a light box that provides stable uniform lighting evenly across the entire base of the light box. A suitable light box is the SANOTO MK50 (Sanoto, Guangdong, China), or equivalent, which provides an illumination of 5500 LUX at a color temperature of 5500K. A Digital Single-Lens Reflex (DSLR) camera with manual setting controls (e.g. a NIKON D40X available from Nikon Inc., Tokyo, Japan, or equivalent) is mounted directly above an opening in the top of the light box so that the entire nonwoven sample and distance scale are visible within the camera's field of view.

Using a standard 18% gray card (e.g., Munsell 18% Reflectance (Gray) Neutral Patch/Kodak Gray Card R-27, available from X-Rite; Grand Rapids, Mich., or equivalent) the camera's white balance is custom set for the lighting conditions inside the light box. The camera's manual settings are set so that the image is properly exposed such that there is no signal clipping in any of the color channels. Suitable settings might be an aperture setting of f/11, an ISO setting of 400, and a shutter speed setting of 1/400 sec. At a focal length of 35 mm the camera is mounted approximately 14 inches above the sample. The image is properly focused, captured, and saved as a JPEG file. The resulting image must contain the entire nonwoven sample and distance scale at a minimum resolution of 15 pixels/mm.

A nonwoven substrate (e.g. 25 gsm BiCo 70:30) is cut into 150 mm×150 mm samples. The samples should be free from wrinkles, tears or other visible defects and care should be taken so as not to contaminate or distort the surface. The nonwoven samples are conditioned at 23° C.±2 C.° and 50%±2% relative humidity for at least 2 hours prior to printing with the hydrophilic coating.

Prepare a suitable hydrophilic coating (e.g. STANTEX S6327, available from Pulcra Chemicals, Rock Hill S.C., diluted with 25% ethanol) with 0.4% Oil Red EGN dye (available from Sigma-Aldrich, St. Louis Mo., or equivalent) added as a colorant to enable visibility of the printed pattern. The hydrophilic coating solution is filtered through a 0.45 um syringe filter (e.g. ACRODISC CR 25 mm PTFE membrane, available from VWR International, or equivalent) to remove any particulates present.

In this example, a 5 mm by 80 mm striped pattern of hydrophilic coating is printed onto the nonwoven substrate using an ink jet printer. A total of 5 replicate samples are prepared for each nonwoven/hydrophilic coating combination for each aging condition to be tested. The nonwoven samples printed with a hydrophilic pattern are stored in a room controlled at 23° C.±2 C.° and 50%±2% relative humidity for 24 hours.

Twenty four (24) hours±2 hours after printing, the initial width ($W_i$) of the hydrophilic coating stripe is measured on a photographic image captured of the nonwoven. Place the nonwoven sample horizontally flat, with the printed side facing upward, on the matte surface within the light box along with the distance scale and capture an image. To analyze the image, transfer it onto a computer running an image analysis software (e.g. Image J, distributed by the National Institute of Health, or equivalent). The image resolution is calibrated using the calibrated distance scale in the image to determine the number of pixels per millimeter. Measure the width of the hydrophilic coating stripe to the nearest 0.01 mm. In like fashion, collect images of an additional 4 substantially similar replicate samples and obtain the width of the hydrophilic coating stripe on each. Calculate the arithmetic mean of the width and report $W_i$ to the nearest 0.01 mm.

After collecting $W_i$, each sample printed with the hydrophilic coating is placed between aluminum foil sheets and stored in a room controlled at 40° C.±2 C.° and 75%±2% relative humidity to age for 1 month (e.g. 4 weeks). After 1 month, 5 replicates of each pattern-printed sample are pulled and equilibrated in a room controlled at 23° C.±2 C.° and 50%±2% relative humidity for 2-4 hours prior to testing.

To assess dry migration, the width of the hydrophilic coating stripe on the aged nonwoven sample ($W_a$) is measured on a photographic image captured and analyzed in the same manner described for measuring the initial width of the printed stripe. A total of 5 substantially similar replicate samples are measured. Calculate the arithmetic mean of the width and report $W_a$ to the nearest 0.01 mm.

The distance a fluid spreads across the printed hydrophilic coating stripe on the aged nonwoven is used to assess wet migration. The test fluid is 0.9% NaCl aqueous dyed blue (e.g. 0.2 wt % methylene blue) to enable better visibility. After measuring $W_a$, the aged pattern-printed nonwoven sample is positioned horizontally with the printed side facing up and secured in such a way that it lies flat but unstrained, and any interaction between the test fluid and the underlying surface is avoided to prevent undue capillary forces. A suitable way to position the sample is to elevate the surface of the pattern-printed nonwoven, securing the edges without straining the sample so that the surface directly underneath the printed stripe is air. Place the suspended nonwoven sample over the matte surface within the light box along with the distance scale. Ensure the distance scale is positioned at the same height as the sample. A 35 uL drop of test fluid is placed onto the hydrophilic coating stripe at its longitudinal and lateral midpoint. Two additional 35 uL drops are placed onto the hydrophilic coating stripe, one on each side of the initial drop, at a distance of about 20 mm from the initial drop. Wait 30 seconds. As previously described herein, capture a photographic image and prep it for analysis. The width of the fluid ($W_{f,a}$) is measured as the maximum distance of fluid spread perpendicularly across the printed stripe of hydrophilic coating. A total of 5 substantially similar replicate samples are measured. Calculate the arithmetic mean of the fluid width and report $W_{f,a}$ to the nearest 0.01 mm.

Calculate Dry Migration ($M_{dry}$) as the ratio of the initial width ($W_i$) of the printed stripe of hydrophilic coating to the width of the printed stripe of hydrophilic coating on the aged nonwoven ($W_a$). Report $M_{dry}$ to the nearest 0.01 mm.

$$M_{dry}=W_a/W_i \text{(exemplified in Table 1 by column Dry 1M)}$$

Calculate Wet Migration Aged ($M_{wet}$ A) as the ratio of the initial width ($W_i$) of the printed stripe of hydrophilic coating to the width of the fluid ($W_{f,A}$) on the aged nonwoven printed with the hydrophilic coating. Report $M_{wet}$ to the nearest 0.01 mm.

$$M_{wet}=W_{f,a}/W_i \text{ (exemplified in Table 1 by column Aged Wet)}$$

One can also calculate the initial migration of the hydrophilic coating upon wetting the sample ($M_{wet\,I}$) by dividing an initial width of the fluid ($W_{f,I}$), calculated as described above but with a fresh sample, by the initial width of the printed stripe of hydrophilic coating ($W_i$):

$$M_{wet\,I}=W_{f,I}/W_i$$

Hydrophilic Pattern Detection & DRY Migration Method for Finished Products

To determine the presence of a hydrophilic pattern (e.g. printed surfactant) on the outermost body facing layer (i.e. topsheet) of an absorbent article in the dry state, the layer is excised from the absorbent article and analyzed using ToF-SIMS. If a hydrophilic pattern is detected, a dry migration test is performed. Dry migration is assessed by comparing the overall area of the initial hydrophilic pattern to the overall area of the pattern on an aged test sample using image analysis. Test samples are conditioned at 23° C.±2 C.° and 50%±2% relative humidity for 2 hours prior to testing and all testing is performed under these same environmental conditions.

Time-of-Flight-Secondary Ion Mass Spectrometry (ToF-SIMS) may be used to evaluate the distribution and migration of actives on film or nonwoven surfaces. ToF-SIMS provides semi-quantitative mass spectrum and image analysis of surfactant distribution on the outermost 3 nm of the test specimen's surface. The overall area of the entire hydrophilic pattern is measured across the entire topsheet excised from the absorbent article. Thus it is ideal that the instrument has a large field of view (e.g. 6 cm×6 cm) so that minimal sectioning of the topsheet test sample is required if the test sample is larger than the field of view. A suitable ToF-SIMS instrument is the TOF.SIMS 5 available from ION TOF (Munster, Germany), or equivalent.

Obtain an absorbent article that is no more than 6 months old. The lot code is used to determine the production date of the product. Remove the absorbent article from its wrapper, if present. To obtain a test sample, excise the entire topsheet from the absorbent article, using care to not impart any contamination or distortion to the layer during the process. A cryogenic spray (such as Quick-Freeze, Miller-Stephenson Company, Danbury, Conn.) can be used to remove the test sample from the underlying layers if necessary.

The measurement of the entire topsheet test sample excised from the absorbent article can be accommodated by cutting the test sample into sections (test specimens), analyzing consecutively under the same instrument conditions and re-stitching the test specimen images together via post-measurement analysis to create one image of the entire topsheet test sample. Thus, if the topsheet test sample is larger than the field of view, cut it into appropriately sized test specimens (e.g. no larger than the instrument's field of view, noting the location of each (e.g. front left, back right, etc) to enable subsequent image re-stitching. The test specimen is mounted as flat as possible onto the ToF-SIMS instrument sample holder via double sided tape (non-outgassing to be compatible with the high vacuum system, such as Scotch repositionable tape by 3M, USA). Avoid contaminating the top surfaces during the sample preparation process. After mounting, the test specimen is then pumped into the high vacuum ToF-SIMS system ($<1\times10^{-8}$ torr) for mass spectrum and image measurement using a 30 keV $Bi_3^+$ primary ion beam. Static ToF-SIMS analysis (primary ion fluences<threshold ($1\times10^{13}$ ions $cm^{-2}$)) using "bunched mode" of the ToF-SIMS instrument is achieved by controlling the target current of the primary beam (typically ~0.3 pA) and with a pre-buncher pulse width of 30 ns. Low energy electrons (~20 eV) need to be supplied by a pulsed electron flood gun for charge compensation due to the insulating nature of the topsheet. In order to make the data comparable within a study consisting of multiple samples and test specimens, all measurements need to be performed under the same instrument conditions. Characteristic signals (positive mode or negative mode) for representing the surfactant species deposited on the test specimen is uniquely selected by either collecting the mass spectrum of the known surfactant raw materials or comparing the mass spectra between the test specimen surface with and without surfactant deposition. Macro image analysis is performed to map the chemical distribution of the selected surfactant signals on the desired field of view (e.g. up to 6 cm×6 cm per measurement, or stitch multiple macro images together to create one image that includes the entire topsheet test sample).

To directly compare the surfactant intensity between samples, all the selected secondary ion images with pre-identified surfactant signals are to be normalized to the total ion intensity within each sample. Set an accurate distance scale based on the known size of the field of view or respective sample size using the software provided along with the instrument (e.g. ION TOF software (SurfaceLab 6), or equivalent). Save the image as a JPEG file. Note the resolution of the resulting image (must have a minimum resolution of 15 pixels/mm).

In like fashion, excise and analyze an additional 4 replicate topsheet test samples and save each as a JPEG file. All replicates must have the same image resolution. Proceed to the Image Analysis Method for Finished Products to process these DRY INITIAL test samples.

To assess dry migration, a subsequent set of replicate absorbent articles are stored in a room controlled at 40° C.±2 C.° and 75%±2% relative humidity to age for 4 weeks. After 4 weeks, 5 replicates of each absorbent article are pulled and equilibrated in a room controlled at 23° C.±2 C.° and 50%±2% relative humidity for 2-4 hours prior to testing. Excise and analyze (via ToF-SIMS) the topsheet test samples from the aged absorbent articles in like fashion to the DRY INITIAL samples and create one image for each entire topsheet test sample. Save the images as JPEG files ensuring the same resolution used for the initial samples, and proceed to the Image Analysis Method for Finished Products to process these DRY AGED test samples.

Hydrophilic Pattern Detection & WET Migration Method for Finished Products

To determine the presence of a hydrophilic pattern (e.g. printed surfactant) on the outermost body facing layer (i.e. topsheet) of an absorbent article in the wet state, the layer is excised from the absorbent article and placed on the surface of colored water. If a hydrophilic pattern is detected, a wet migration test is performed. Wet migration is assessed by comparing the area of the initial hydrophilic pattern to the area of the pattern on an aged test sample using image analysis. Test samples are conditioned at 23° C.±2 C.° and 50%±2% relative humidity for 2 hours prior to testing and all testing is performed under these same environmental conditions.

After exposing a test sample to colored water as described below, the test sample is suspended horizontally flat over a matte white background inside a light box that provides stable uniform lighting evenly across the entire base of the light box. A suitable light box is the Sanoto MK50 (Sanoto, Guangdong, China), or equivalent, which provides an illumination of 5500 LUX at a color temperature of 5500K. The illumination and color temperature are verified using a light meter prior to capturing images inside the light box to ensure the lighting conditions are consistent between each image obtained. A suitable light meter is the CL-70F CRI Illuminance Meter available from Konica Minolta, or equivalent. A Digital Single-Lens Reflex (DSLR) camera with manual setting controls (e.g. a NIKON D40X available from Nikon Inc., Tokyo, Japan, or equivalent) is mounted directly above an opening in the top of the light box so that the entire test sample is visible within the camera's field of view.

Using a standard 18% gray card (e.g., Munsell 18% Reflectance (Gray) Neutral Patch/Kodak Gray Card R-27, available from X-Rite; Grand Rapids, Mich., or equivalent) the camera's white balance is custom set for the lighting conditions inside the light box. The camera's manual settings are set so that the image is properly exposed such that there is no signal clipping in any of the color channels. Suitable settings might be an aperture setting of f/11, an ISO setting of 400, and a shutter speed setting of 1/400 sec. At a focal length of 35 mm the camera is mounted approximately 14 inches above the sample. The image is properly focused, captured, and saved as a JPEG file. The resulting image must contain the entire test sample at a minimum resolution of 15 pixels/mm. The sample image is distance calibrated against an image of a ruler (certified by NIST) acquired at the same focal length and resolution as the test sample.

Obtain an absorbent article that is no more than 6 months old. The lot code is used to determine the production date of the product. Remove the absorbent article from its wrapper, if present, and make a mark on the topsheet about 3 mm inboard at each longitudinal end. Measure the distance between the two marks and record as the gage length to the nearest 1 mm. To obtain a test sample, excise the entire topsheet from the article, using care to not impart any contamination or distortion to the layer during the process. A cryogenic spray (such as Quick-Freeze, Miller-Stephenson Company, Danbury, Conn.) can be used to remove the test sample from the underlying layers if necessary. Prepare the test liquid by adding 0.05 wt % methylene blue dye (available from VWR International), or equivalent, to deionized water. The test sample is exposed to the colored test liquid as follows.

Obtain a shallow dish large enough to allow the entire test sample to lie horizontally flat inside. Obtain a total of 6 bars that are about 3 mm tall, no more than 25 mm wide and the length is similar to the width (lateral edge to lateral edge) of the test sample. The bars are made of stainless steel (or equivalent) and heavy enough to sufficiently hold the test sample in place. The test sample is attached to two of the bars. Two bars will be used as risers in the dish of liquid and the other two bars will be used as risers in the light box.

Place the test sample on a horizontally flat surface with the garment side facing up. Using double sided tape that is about 3 mm wide, secure the test sample to the bottom surface of two bars immediately outboard of the two gage marks. Adjust the distance between the test sample bars such that the distance between them is equal to the gage length. Place one riser at each end of the shallow dish such that the distance between them is equal to the gage length. Fill the dish with the colored test liquid to a depth equal to the height of the risers. Carefully transfer the test sample to the dish of colored test liquid and place the bars onto the risers in the dish such that the body facing surface of the test sample makes contact with the surface of the colored test liquid. Any hydrophilic areas on the test sample will become notably colored (e.g. blue) within 10 seconds due to wetting by the colored test liquid. If a hydrophilic pattern is not detected, the test is over. After 10 seconds, if a hydrophilic pattern is detected, carefully transfer the test sample (still attached to two bars) from the colored liquid to a sheet of blotting paper (e.g. Whatman grade 1, available from VWR International) that is the same size or larger than the test sample. Allow the body facing surface of the test sample to make contact with the blotting paper for no more than 3 seconds to remove any droplets of test liquid from the back surface. Place 2 risers on the matte white surface inside the light box such that the distance between them is equal to the gage length. Carefully transfer the test sample to the light box and place the bars onto the risers, thereby suspending it horizontally flat over the matte white surface. Capture an image of the entire test sample. Remove the test sample from the light box. Place a distance scale (certified by NIST) horizontally flat on top of the risers inside of the light box and capture an image at the same focal length and resolution as that used for the test sample. This is the calibration image.

In like fashion, analyze an additional 4 replicate topsheet test samples and save each as a JPEG file. Proceed to the Image Analysis Method for Finished Products to process these WET INITIAL test samples.

To assess wet migration, a subsequent set of replicate absorbent articles are stored in a room controlled at 40° C.±2 C.° and 75%±2% relative humidity to age for 4 weeks. After 4 weeks, 5 replicates of each absorbent article are pulled and equilibrated in a room controlled at 23° C.±2 C.° and 50%±2% relative humidity for 2-4 hours prior to testing. Excise and analyze the topsheet test samples from the aged absorbent articles in like fashion to the WET INITIAL samples. Ensure the lighting conditions, focal length and image resolution are the same as those used for the WET INITIAL test samples. Save the images as JPEG files and proceed to the Image Analysis Method for Finished Products to process these WET AGED test samples.

Image Analysis Method for Finished Products

To analyze the images, transfer them onto a computer running an image analysis software (e.g. Image J, distributed by the National Institute of Health, or equivalent). The test sample image is opened in the image analysis program and the distance scale is set using the distance calibration to determine the number of pixels per millimeter. For the DRY test samples, the distance calibration is done using the distance scale within the image. For the WET test samples, the calibration image is opened in the image analysis program and a linear distance calibration is performed using the image of the distance scale. The test sample image is then cropped, if necessary, to include only the test sample (e.g. exclude the bars used to hold the WET samples). Convert the image to 8-bit grayscale. Threshold to a value that separates the regions containing the hydrophilic pattern (e.g. regions of intensity detected by ToF-SIMS for the DRY samples and regions stained by the colored test liquid for the WET samples) from the regions that are not part of the hydrophilic pattern to generate a binary image. In the binary image, "zero" or "black" corresponds to the hydrophilic pattern. See FIGS. 16A, 16B, 17A and 17B for examples. Note the threshold value so that it can be used on subsequent images of the same test sample type (e.g. DRY or WET). In the binary image, measure the total area of the hydrophilic pattern (e.g. lines, shapes, outlines that represent intensified or stained regions) on the test sample and report to the nearest 0.01 square mm, noting whether the sample is DRY INITIAL, DRY AGED, WET INITIAL or WET AGED. In like fashion, analyze the images of all replicates for each type of sample and obtain the overall area of the hydrophilic pattern on each. Calculate the arithmetic mean of the overall area measured for each type of sample and report to the nearest 0.01 square mm as follows:

DRY INITIAL Area ($A_{DRY, i}$) and DRY AGED Area ($A_{DRY, a}$)

WET INITIAL Area ($A_{WET, i}$) and WET AGED Area ($A_{WET, a}$)

Calculate the percentage of DRY Migration ($M_{DRY}$) as the % difference between the DRY AGED Area and DRY INITIAL Area of the hydrophilic pattern. Report $M_{DRY}$ to the nearest 0.1%.

$$\%M_{DRY}=[(A_{DRY,a}-A_{DRY,i})/A_{DRY,i}]*100$$

Calculate the percentage of WET Migration ($M_{WET}$) as the % difference between the WET AGED Area and WET INITIAL Area of the hydrophilic pattern. Report $M_{WET}$ to the nearest 0.1%.

$$\%M_{WET}=[(A_{WET,a}-A_{WET,i})/A_{WET,i}]*100$$

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A wearable absorbent article comprising:
    a liquid pervious topsheet, said topsheet having an outward-facing topsheet surface and a wearer-facing topsheet surface, wherein at least a portion of the topsheet has been rendered hydrophobic via melt additive or surface treatment;
    a backsheet joined to said topsheet, said backsheet having a wearer-facing backsheet surface and an outward-facing backsheet surface; and
    an absorbent core disposed between said topsheet and said backsheet, said absorbent core having a wearer-facing core surface and an outward-facing core surface;
    wherein a hydrophilic surfactant is applied to at least a portion of said wearer-facing topsheet surface, and wherein the hydrophilic surfactant is applied over the areas of the topsheet previously rendered hydrophobic.

2. The absorbent article of claim 1, wherein the topsheet comprises hydrophobic and hydrophilic zones, wherein the hydrophilic zones comprise hydrophilic surfactant placed on areas having hydrophobic treatments.

3. The absorbent article of claim 1, wherein the surfactant is nonionic, cationic, anionic or combinations thereof.

4. The absorbent article of claim 1, wherein the surfactant comprises a PEG diester having a carbon chain of $C_{12}$ or greater.

5. The absorbent article of claim 1, wherein the surfactant comprises a $C_{12}$ or greater alcohol ethoxylates or PEG diesters.

6. The absorbent article of claim 1, wherein the surfactant comprises a PEG group that is at least 5 ethylene oxide units.

7. The absorbent article of claim 6, wherein the surfactant comprises a PEG group that is between 6 ethylene oxide groups and 20 ethylene oxide groups.

8. The absorbent article of claim 1, wherein the surfactant comprises a blend having greater than 50% $C_{12}$ or greater chain length.

9. The absorbent article of claim 1, wherein the surfactant comprises an ethoxylated derivative containing a hydroxyl acid alkyl chain.

10. The absorbent article of claim 1, wherein the topsheet is rendered hydrophobic by a treatment selected from the group consisting of petroleum-based hydrocarbons having from about 4 to about 32 carbon atoms, fatty alcohols having from about 12 to about 24 carbon atoms, polysiloxane compounds, fatty acid esters, alkyl ethoxylates, fatty alcohol ethers having from about 12 to about 28 carbon atoms in their fatty chain, lanolin and its derivatives, glyceride derivatives including acetoglycerides and ethoxylated glycerides of C12-C28 fatty acids, fatty amides, and combinations thereof.

11. The absorbent article of claim 1, wherein the topsheet is rendered hydrophobic by a treatment selected from the group consisting of amides, tryglicerides, functional silicones, or combinations thereof.

* * * * *